(12) United States Patent
Greenberg et al.

(10) Patent No.: US 11,406,388 B2
(45) Date of Patent: Aug. 9, 2022

(54) ROTATABLE DEVICE AND METHOD FOR FIXING TRICUSPID VALVE TISSUE

(71) Applicant: Evalve, Inc., Santa Clara, CA (US)

(72) Inventors: Jacob L. Greenberg, Menlo Park, CA (US); Koji J. Kizuka, San Francisco, CA (US)

(73) Assignee: Evalve, Inc., Santa Clara, CA (US)

( * ) Notice: Subject to any disclaimer, the term of this patent is extended or adjusted under 35 U.S.C. 154(b) by 574 days.

(21) Appl. No.: 16/260,564

(22) Filed: Jan. 29, 2019

(65) Prior Publication Data

US 2019/0150926 A1 May 23, 2019

Related U.S. Application Data

(62) Division of application No. 15/377,793, filed on Dec. 13, 2016, now Pat. No. 10,314,586.

(51) Int. Cl.
*A61B 17/08* (2006.01)
*A61B 17/04* (2006.01)
(Continued)

(52) U.S. Cl.
CPC ...... *A61B 17/083* (2013.01); *A61B 17/00234* (2013.01); *A61B 17/0401* (2013.01);
(Continued)

(58) Field of Classification Search
CPC .... A61F 2/2427; A61F 2/2442; A61F 2/2454; A61F 2/2466; A61F 2/2463;
(Continued)

(56) References Cited

U.S. PATENT DOCUMENTS 2,097,018 A 10/1937 Chamberlain
2,108,206 A 2/1938 Meeker
(Continued)

FOREIGN PATENT DOCUMENTS

DE 3504292 C1 7/1986
DE 101 16 168 A1 11/2001
(Continued)

OTHER PUBLICATIONS

U.S. Appl. No. 15/377,793, filed Dec. 13, 2016 (Jun. 11, 2019).
(Continued)

*Primary Examiner* — Richard G Louis
*Assistant Examiner* — Chima U Igboko
(74) *Attorney, Agent, or Firm* — Baker Botts L.L.P.

(57) ABSTRACT

The present disclosure relates to repair devices, repair systems, and methods for repair of regurgitant tricuspid valves. A repair method includes positioning a repair device at a tricuspid valve. The repair device includes a pair of proximal arms and a pair of corresponding opposing distal arms, with each proximal arm and corresponding opposite distal arm forming an arm pair. The arms are actuated so that leaflet tissue is grasped between the proximal and distal arms, with a first leaflet being grasped by a first arm pair and a second leaflet being grasped by a second arm pair. A suture line is anchored at the second leaflet. Then, the repair device is pivoted to grasp and suture a third tricuspid leaflet to tie the second and third leaflets together. The clip remains deployed to tie the first and third leaflets together.

26 Claims, 14 Drawing Sheets

(51) Int. Cl.
*A61B 17/00* (2006.01)
*A61F 2/24* (2006.01)
*A61B 17/122* (2006.01)
*A61B 17/128* (2006.01)
*A61B 17/06* (2006.01)

(52) U.S. Cl.
CPC ........ *A61B 17/0469* (2013.01); *A61B 17/122* (2013.01); *A61B 17/1285* (2013.01); *A61F 2/2463* (2013.01); *A61F 2/2466* (2013.01); *A61B 17/0482* (2013.01); *A61B 2017/00243* (2013.01); *A61B 2017/00349* (2013.01); *A61B 2017/00783* (2013.01); *A61B 2017/0404* (2013.01); *A61B 2017/0406* (2013.01); *A61B 2017/0409* (2013.01); *A61B 2017/0417* (2013.01); *A61B 2017/0464* (2013.01); *A61B 2017/0472* (2013.01); *A61B 2017/0488* (2013.01); *A61B 2017/06052* (2013.01); *A61B 2017/081* (2013.01)

(58) Field of Classification Search
CPC ............ A61B 17/0469; A61B 17/0482; A61B 2017/00783; A61B 2017/0404; A61B 2017/0406; A61B 2017/0409; A61B 2017/0472; A61B 2017/0488; A61B 17/083; A61B 17/00234; A61B 17/0401; A61B 17/122; A61B 17/1285; A61B 2017/00243; A61B 2017/00349; A61B 2017/0417; A61B 2017/0464; A61B 2017/06052; A61B 2017/081
See application file for complete search history.

(56) References Cited

U.S. PATENT DOCUMENTS

| | | |
|---|---|---|
| 3,296,668 A | 1/1967 | Aiken |
| 3,378,010 A | 4/1968 | Codling et al. |
| 3,557,780 A | 1/1971 | Sato |
| 3,675,639 A | 7/1972 | Cimber |
| 3,874,388 A | 4/1975 | King et al. |
| 4,007,743 A | 2/1977 | Blake |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,458,682 A | 7/1984 | Cerwin |
| 4,425,908 A | 11/1984 | Simon |
| 4,487,205 A | 12/1984 | Di Giovanni et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,944,295 A | 7/1990 | Gwathmey et al. |
| 4,969,890 A | 11/1990 | Sugita et al. |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,108,368 A | 4/1992 | Hammerslag et al. |
| 5,125,758 A | 6/1992 | DeWan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Kreuter et al. |
| 5,368,564 A | 11/1994 | Savage |
| 5,368,601 A | 11/1994 | Sauer et al. |
| 5,383,886 A | 1/1995 | Kensey et al. |
| 5,391,182 A | 2/1995 | Chin |
| 5,403,312 A | 4/1995 | Yates et al. |
| 5,403,326 A | 4/1995 | Harrison et al. |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,562,678 A | 10/1996 | Booker |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup, III |
| 5,593,435 A | 1/1997 | Carpentier et al. |
| 5,609,598 A | 3/1997 | Laufer et al. |
| 5,618,306 A | 4/1997 | Roth et al. |
| 5,620,452 A | 4/1997 | Yoon |
| 5,620,461 A | 4/1997 | Muijs Van De Moer et al. |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mari et al. |

(56) References Cited

U.S. PATENT DOCUMENTS

| | | |
|---|---|---|
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keital et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racene et al. |
| 5,715,817 A | 2/1998 | Stevens-Wright et al. |
| 5,716,367 A | 2/1998 | Koike et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,749,828 A | 5/1998 | Solomon et al. |
| 5,759,193 A | 6/1998 | Burbank et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,955 A | 10/1998 | Kuck et al. |
| 5,824,065 A | 10/1998 | Gross |
| 5,827,237 A | 10/1998 | Macoviak et al. |
| 5,833,671 A | 11/1998 | Macoviak et al. |
| 5,836,955 A | 11/1998 | Buelna et al. |
| 5,843,031 A | 12/1998 | Hermann et al. |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,860,990 A | 1/1999 | Nobles et al. |
| 5,861,003 A | 1/1999 | Latson et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,143,024 A | 11/2000 | Campbell et al. |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,182,664 B1 | 2/2001 | Cosgrove |
| 6,187,003 B1 | 2/2001 | Buysse et al. |
| 6,190,408 B1 | 2/2001 | Melvin |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,461,366 B1 | 10/2002 | Seguin |
| 6,464,707 B1 | 10/2002 | Bjerken |
| 6,475,230 B1 * | 11/2002 | Bonutti ............... A61B 17/0487 606/232 |
| 6,482,224 B1 | 11/2002 | Mi et al. |
| 6,485,489 B2 | 11/2002 | Teirstein et al. |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |

(56) References Cited

U.S. PATENT DOCUMENTS

| | | |
|---|---|---|
| 6,702,826 B2 | 3/2004 | Liddicoat et al. |
| 6,709,382 B1 | 3/2004 | Homer |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,048,754 B2 | 5/2006 | Martin et al. |
| 7,112,207 B2 | 9/2006 | Allen et al. |
| 7,226,467 B2 | 6/2007 | Lucatero et al. |
| 7,288,097 B2 | 10/2007 | Seguin |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hilavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thorton et al. |
| 2004/0093023 A1* | 5/2004 | Allen ............... A61B 17/0482 606/213 |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Lai et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goar et al. |
| 2005/0021057 A1 | 1/2005 | St. Goar et al. |

(56) References Cited

U.S. PATENT DOCUMENTS

| | | |
|---|---|---|
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0020275 A1 | 1/2006 | Goldfarb et al. |
| 2006/0030866 A1 | 2/2006 | Schreck |
| 2006/0030867 A1* | 2/2006 | Zadno ............ A61B 17/0644 606/142 |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1* | 4/2006 | Goldfarb ............ A61B 17/1285 606/215 |
| 2006/0089711 A1 | 4/2006 | Dolan |
| 2006/0135993 A1 | 6/2006 | Seguin |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Randert et al. |
| 2007/0038293 A1 | 2/2007 | St. Goar et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0198082 A1 | 8/2007 | Kapadia et al. |
| 2008/0033425 A1* | 2/2008 | Davis ............ A61B 17/0057 606/41 |
| 2008/0039935 A1 | 2/2008 | Buch et al. |
| 2008/0051703 A1 | 2/2008 | Thornton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goar et al. |
| 2008/0183194 A1 | 7/2008 | Goldfarb et al. |
| 2009/0156995 A1 | 6/2009 | Martin et al. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goar et al. |
| 2014/0236198 A1 | 8/2014 | Goldfarb et al. |
| 2016/0045314 A1* | 2/2016 | Keren ............ A61F 2/2442 623/2.36 |
| 2016/0174979 A1 | 6/2016 | Wei |
| 2018/0021133 A1* | 1/2018 | Barbarino ............ A61F 2/2463 623/2.37 |

FOREIGN PATENT DOCUMENTS

| | | |
|---|---|---|
| EP | 0 179 562 B1 | 7/1989 |
| EP | 0 558 031 B1 | 2/1993 |
| EP | 0 684 012 A2 | 11/1995 |
| EP | 0 727 239 A2 | 8/1996 |
| EP | 0 782 836 A1 | 7/1997 |
| EP | 1 230 899 A1 | 8/2002 |
| EP | 1 674 040 A2 | 6/2006 |
| FR | 2 768 324 A1 | 3/1999 |
| GB | 1 598 111 A | 9/1981 |
| GB | 2 151 142 A | 7/1985 |
| JP | 09-253030 A | 9/1997 |
| JP | 11-089937 A | 4/1999 |
| JP | 2000-283130 A | 10/2000 |
| JP | 2015-502548 | 1/2015 |
| WO | WO 81/00668 A1 | 3/1981 |
| WO | WO 91/18881 A1 | 12/1991 |
| WO | WO 92/12690 A1 | 8/1992 |
| WO | WO 94/18881 A1 | 9/1994 |
| WO | WO 94/18893 A1 | 9/1994 |
| WO | WO 95/11620 A2 | 5/1995 |
| WO | WO 95/15715 A1 | 6/1995 |
| WO | WO 96/14032 A1 | 5/1996 |
| WO | WO 96/20655 A1 | 7/1996 |
| WO | WO 96/2273 5 A1 | 8/1996 |
| WO | WO 96/30072 A1 | 10/1996 |
| WO | WO 97/18746 A2 | 5/1997 |
| WO | WO 97/25927 A1 | 7/1997 |
| WO | WO 97/26034 A1 | 7/1997 |
| WO | WO 97/38748 A2 | 10/1997 |
| WO | WO 97/39688 A2 | 10/1997 |
| WO | WO 97/48436 A2 | 12/1997 |
| WO | WO 98/07375 A1 | 2/1998 |
| WO | WO 98/24372 A1 | 6/1998 |
| WO | WO 98/30153 A1 | 7/1998 |
| WO | WO 98/32382 A1 | 7/1998 |
| WO | WO 99/07354 A2 | 2/1999 |
| WO | WO 99/13777 A1 | 3/1999 |
| WO | WO 00/02489 A1 | 1/2000 |
| WO | WO 00/03651 A1 | 1/2000 |
| WO | WO 00/003759 A2 | 1/2000 |
| WO | WO 00/12168 A1 | 3/2000 |
| WO | WO 00/44313 A1 | 8/2000 |
| WO | WO 00/59382 A1 | 10/2000 |
| WO | WO 01/00111 A1 | 1/2001 |
| WO | WO 01/00114 A1 | 1/2001 |
| WO | WO 01/03651 A2 | 1/2001 |
| WO | WO 01/26557 A1 | 4/2001 |
| WO | WO 01/26586 A1 | 4/2001 |
| WO | WO 01/26587 A1 | 4/2001 |
| WO | WO 01/26588 A2 | 4/2001 |
| WO | WO 01/26703 A1 | 4/2001 |
| WO | WO 01/28432 A1 | 4/2001 |
| WO | WO 01/28455 A1 | 4/2001 |
| WO | WO 01/47438 A1 | 7/2001 |
| WO | WO 01/49213 A2 | 7/2001 |
| WO | WO 01/50985 A1 | 7/2001 |
| WO | WO 01/54618 A1 | 8/2001 |
| WO | WO 01/56512 A1 | 8/2001 |
| WO | WO 01/66001 A2 | 9/2001 |
| WO | WO 01/70320 A1 | 9/2001 |
| WO | WO 01/89440 A2 | 11/2001 |
| WO | WO 01/95831 A2 | 12/2001 |
| WO | WO 01/95832 A2 | 12/2001 |
| WO | WO 01/97741 A2 | 12/2001 |
| WO | WO 02/00099 A2 | 1/2002 |
| WO | WO 02/01999 A2 | 1/2002 |
| WO | WO 02/03892 A1 | 1/2002 |
| WO | WO 02/34167 A2 | 5/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 03/001893 A2 | 1/2003 |
| WO | WO 03/003930 A1 | 1/2003 |
| WO | WO 03/020179 A1 | 3/2003 |
| WO | WO 03/028558 A2 | 4/2003 |
| WO | WO 03/037171 A2 | 5/2003 |
| WO | WO 03/047467 A1 | 6/2003 |
| WO | WO 03/049619 A2 | 6/2003 |
| WO | WO 03/073910 A2 | 9/2003 |
| WO | WO 03/073913 A2 | 9/2003 |
| WO | WO 03/082129 A2 | 10/2003 |
| WO | WO 03/105667 A2 | 12/2003 |
| WO | WO 2004/004607 A1 | 1/2004 |
| WO | WO 2004/012583 A2 | 2/2004 |
| WO | WO 2004/012789 A2 | 2/2004 |
| WO | WO 2004/014282 A2 | 2/2004 |
| WO | WO 2004/019811 A2 | 3/2004 |
| WO | WO 2004/030570 A2 | 4/2004 |

(56) References Cited

FOREIGN PATENT DOCUMENTS

| WO | WO 2004/037317 A2 | 5/2004 |
| --- | --- | --- |
| WO | WO 2004/045370 A2 | 6/2004 |
| WO | WO 2004/045378 A2 | 6/2004 |
| WO | WO 2004/045463 A2 | 6/2004 |
| WO | WO 2004/047679 A1 | 6/2004 |
| WO | WO 2004/062725 A1 | 7/2004 |
| WO | WO 2004/082523 A2 | 9/2004 |
| WO | WO 2004/082538 A2 | 9/2004 |
| WO | WO 2004/093730 A2 | 11/2004 |
| WO | WO 2004/112585 A2 | 12/2004 |
| WO | WO 2004/112651 A2 | 12/2004 |
| WO | WO 2005/002424 A2 | 1/2005 |
| WO | WO 2005/018507 A2 | 3/2005 |
| WO | WO 2005/027797 A1 | 3/2005 |
| WO | WO 2005/032421 A2 | 4/2005 |
| WO | WO 2005/062931 A2 | 7/2005 |
| WO | WO 2005/112792 A2 | 12/2005 |
| WO | WO 2006/037073 A2 | 4/2006 |
| WO | WO 2006/105008 A1 | 10/2006 |
| WO | WO 2006/105009 A1 | 10/2006 |
| WO | WO 2006/115875 A2 | 11/2006 |
| WO | WO 2006/115876 A2 | 11/2006 |
| WO | WO 2016/110760 A1 | 7/2016 |

OTHER PUBLICATIONS

U.S. Appl. No. 15/377,793, filed Jan. 29, 2019 Issue Fee Payment.
U.S. Appl. No. 15/377,793, filed Nov. 1, 2018 Notice of Allowance.
U.S. Appl. No. 15/377,793, filed Sep. 28, 2018 Request for Continued Examination (RCE).
U.S. Appl. No. 15/377,793, filed Aug. 24, 2018 Notice of Allowance.
U.S. Appl. No. 15/377,793, filed May 30, 2018 Response to Restriciton Requirement.
U.S. Appl. No. 15/377,793, filed Apr. 5, 2018 Restriciton Requirement.
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The Edge to Edge Technique," The European Association For Cardio-Thoracic Surgery, 14th Annual Meeting, Frankfurt / Germany, Oct. 7-11, 2000, Post Graduate Courses, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Arisi et al., "Mitral Valve Repair with Alfieri Technique in Mitral Regurgitation of Diverse Etiology: Early Echocardiographic Results," Circulation Supplement II, 104(17):3240 (2001).
Bailey, "Mitral Regurgitation" in Surgery of the Heart, Chapter 20, pp. 686-737 (1955).
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia et al., "Edge-to-edge Mitral Repair: A Versatile Mitral Repair," http://www.sts.org/doc/7007 accessed on Sep. 24, 2008.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action dated Sep. 9, 2013 in Application No. 200980158707.2 (with English translation).
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).
Frazier et al., "Early Clinical Experience with an Implantable, Intracardiac Circulatory Support Device: Operative Considerations and Physiologic Implications," http://www.sts.org/doc7007 accessed on Sep. 24, 2008.
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene et al., "Early and late postoperative results of mitral and tricuspid valve insufficiency surgical treatment using edge-to-edge central coaptation procedure," Medicina (Kaunas) 38(Suppl. 2):172-175 (2002).
Gatti et al., "The edge to edge technique as a trick to rescue an imperfect mitral valve repair," Eur. J. Cardiothorac Surg, 22:817-820 (2002).
Gillinov et al., "Is Minimally Invasive Heart Valve Surgery a Paradigm for the Future?" Current Cardiology Reports, 1:318-322 (1999).
Gundry et al., "Facile Mitral Valve Repair Utilizing Leaflet Edge Approximation: Midterm Results of the Alfieri Figure of Eight Repair," The Western Thoracic Surgical Association, Scientific Session (May 1999).
Gupta et al., "Influence of Older Donor Grafts on Heart Transplant Survival: Lack of Recipient Effects," http://www.sts.org/doc/7007 accessed on Sep. 24, 2008.
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
International Search Report and Written Opinion of PCT Application No. PCT/US2009/068023, dated Mar. 2, 2010, 10 pages total.
Izzat et al., "Early Experience with Partial Left Ventriculectomy in the Asia-Pacific Region," Annals of Thoracic Surgery, 67:1703-1707 (1999).
Kallner et al., "Transaortic Approach for the Alfieri Stitch," Ann Thorac Surg, 71:378-380 (2001).
Kavarana et al., "Transaortic Repair of Mitral Regurgitation," The Heart Surgery Forum, #2000-23 89, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Kherani et al., "The Edge-To-Edge Mitral Valve Repair: The Columbia Presbyterian Experience," Ann. Thorac. Surg., 78:73-76 (2004).

(56) References Cited

OTHER PUBLICATIONS

Konertz et al., "Results After Partial Left Ventriculectomy in a European Heart Failure Population," Journal of Cardiac Surgery, 14:129-135 (1999).
Kron et al., "Surgical Relocation of the Posterior Papillary Muscle in Chronic Ischemic Mitral Regurgitation," Annals. of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "'Double-Orifice' Technique to Repair Extensive Mitral Valve Excision Following Acute Endocarditis," J. Card Surg, 13:24-26 (1998).
Lorusso et al., "The double-orifice technique for mitral valve reconstruction: predictors of postoperative outcome," Eur J. Cardiothorac Surg, 20:583-589 (2001).
Maisano et al., "The Double Orifice Repair for Barlow Disease: A Simple Solution for Complex Repair," Circulation 100(18):I-94 (1999).
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).
McCarthy et al., "Partial left ventriculectomy and mitral valve repair for end-stage congestive heart failure," European Journal of Cardio-thoracic Surgery, 13:337-343 (1998).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37:263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al., "Tricuspid Valve Incompetence Caused by Nonpenetrating Thoracic Trauma", Annals of Thoracic Surgery, 51:320-322 (1991).
Osawa et al., "Partial Left Ventriculectomy in a 3-Year Old Boy with Dilated Cardiomyopathy," Japanese Journal of Thoracic and Cardiovascular Surg, 48:590-593 (2000).
Patel et al., "Epicardial Atrial Defibrillation: Novel Treatment of Postoperative Atrial Fibrillation," http://www.sts.org/doc/7007 accessed on Sep. 23, 2008.
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Robicsek et al., "The Bicuspid Aortic Valve. How Does It Function? Why Does It Fail," http://www.sts.org/doc/7007 accessed on Sep. 24, 2008.
Supplemental European Search Report of EP Application No. 02746781, dated May 13, 2008, 3 pages total.
Supplementary European Search Report issued in European Application No. 05753261.6 dated Jun. 9, 2011, 3 pages total.
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., "Annular Geometric Remodeling in Chronic Ischemic Mitral Regurgitation," http://www.sts.org/doc/7007 accessed on Sep. 24, 2008.
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
Umana et al., "'Bow-tie' Mitral Valve Repair Successfully Addresses Subvalvular Dysfunction in Ischemic Mitral Regurgitation," Surgical Forum, XLVIII:279-280 (1997).
Votta et al., "3-D Computational Analysis of the Stress Distribution on the Leaflets after Edge-to-Edge Repair of Mitral Regurgitation," Journal of Heart Valve Disease, 11:810-822 (2002).
U.S. Appl. No. 15/377,793 (US 10,314,586), filed Dec. 13, 2016 (Jun. 11, 2019).
U.S. Appl. No. 15/377,793, filed May 30, 2018 Response to Restriction Requirement.
U.S. Appl. No. 15/377,793, filed Apr. 5, 2018 Restriction Requirement.

* cited by examiner

ROTATABLE DEVICE AND METHOD FOR FIXING TRICUSPID VALVE TISSUE

This application is a divisional of U.S. patent application Ser. No. 15/377,793, filed Dec. 13, 2016, the entire contents of which are incorporated by reference herein.

BACKGROUND

The tricuspid valve controls blood flow from the right atrium to the right ventricle of the heart, preventing blood from flowing backwards from the right ventricle into the right atrium so that it is instead forced through the pulmonary valve and into the pulmonary arteries for delivery to the lungs. A properly functioning tricuspid valve opens and closes to enable blood flow in one direction. However, in some circumstances the tricuspid valve is unable to close properly, allowing blood to regurgitate back into the atrium. Such regurgitation can result in shortness of breath, fatigue, heart arrhythmias, and even heart failure.

Tricuspid valve regurgitation has several causes. Functional tricuspid valve regurgitation (FTR) is characterized by structurally normal tricuspid valve leaflets that are nevertheless unable to properly coapt with one another to close properly due to other structural deformations of surrounding heart structures. Often, the right ventricle is dilated as a result of pulmonary hypertension or an abnormal heart muscle condition (cardiomyopathy).

Other causes of tricuspid valve regurgitation are related to defects of the tricuspid valve leaflets, tricuspid valve annulus, or other tricuspid valve tissues. In some circumstances, tricuspid valve regurgitation is a result of infective endocarditis, blunt chest trauma, rheumatic fever, Marfan syndrome, carcinoid syndrome, or congenital defects to the structure of the heart. Tricuspid valve conditions are also often associated with problems related to the left side of the heart, such as mitral valve regurgitation.

Tricuspid valve regurgitation is often treated by replacing the tricuspid valve with a replacement valve implant or by repairing the valve through an interventional procedure. One method for repairing the tricuspid valve is through annuloplasty. Annuloplasty is accomplished by delivering and implanting a ring or band in the annulus of the tricuspid valve to attempt to return the annulus to a functioning shape. In tricuspid valve repair procedures, a surgeon attempts to reshape or reposition tricuspid valve leaflets so that they can better coapt with one another to sufficiently close the valve and prevent regurgitation.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Certain embodiments described herein are directed to devices and methods for repairing tissue, such as tissue of a malfunctioning cardiac valve, including a regurgitant tricuspid valve. Some embodiments are directed to methods for repairing tissue by positioning a repair device at a targeted location. The repair device includes a pair of distal arms and a pair of corresponding proximal arms disposed opposite the pair of distal arms, each proximal arm and corresponding opposite distal arm forming an arm pair. The repair device is actuated to grasp leaflet tissue of the targeted valve between the proximal and distal arms. A first arm pair grasps tissue at a first engagement point, and a second arm pair grasps tissue at a second engagement point. Preferably, the first and second engagement points are located respectively on first and second adjacent leaflets of a tricuspid valve.

The leaflet tissue at the second engagement point is sutured. For example, one or more suture lines are passed through the leaflet tissue and are anchored at the second engagement point to prevent the one or more suture lines from detaching or tearing away from the second engagement point. In some embodiments, a suturing catheter is positioned near the second arm pair and engages with the second arm pair to enable deployment of the one or more suture lines at the leaflet tissue grasped by the second arm pair.

After deploying the one or more suture lines at the second engagement point, the second arm pair is pivoted to a third engagement point (e.g., the third tricuspid leaflet) while the first arm pair remains engaged at the first engagement point (e.g., the first tricuspid leaflet). The pivoting motion carries the one or more suture lines deployed at the second engagement point (e.g., the second tricuspid leaflet) to the third engagement point. Tension in the one or more suture lines can then be adjusted to tie together the tissue of the second engagement point and third engagement point to a desired degree. The repair device remains deployed across the first and third engagement points to tie together the tissue of the first and third engagement points. The repair device can be adjusted to tie the grasped tissue together to a desired degree.

In certain embodiments, at least a first arm pair of the repair device includes a point element configured to engage against leaflet tissue to function as a pivot point allowing a second arm pair to rotate about the pivot point. In some embodiments, at least the second arm pair includes a set of through holes through which one or more suture lines are passable to enable suturing of leaflet tissue grasped by the second arm pair. In some embodiments, the second arm pair is independently adjustable so that the first arm pair can remain in a closed/grasped configuration during pivoting while the second arm pair is in a more open configuration to allow it to rotate around the first engagement point.

In some embodiments, a heart valve repair system includes a repair device and a suturing catheter. The suturing catheter includes an internal lumen through which one or more suture lines are extendable, the suturing catheter being configured to engage with the second arm pair of the repair device to enable passage of the one or more suture lines through the leaflet tissue grasped by the second arm pair.

In certain embodiments, a repair device includes a proximal member with an axial lumen and a plurality or extendable arms which may be extended to an open position transverse to the axial lumen, and a distal member disposed at least partially within the axial lumen of the proximal member so as to be axially translatable relative to the proximal member. The distal member includes an end section extending distally beyond the proximal member. The end section includes a plurality of extendable arms which are extendable to an open position transverse to an axis of the distal member.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

At least some of the embodiments described herein are directed to devices and methods for repairing a malfunctioning cardiac valve, such as a regurgitant tricuspid valve. Some embodiments are directed to devices and methods configured to provide repair of a regurgitant tricuspid valve through a "lasso" technique capable of tethering and/or tightening the three leaflets of the tricuspid valve together in a desired configuration to improve valve closure and minimize or eliminate regurgitation at the tricuspid valve.

Although many of the examples illustrated and described herein are directed to tricuspid valve regurgitation, it will be understood that the principles, features, and components described herein may also be applied in other applications, such as repair of other heart valves, or use in other interventional procedures or treatment applications.

Figure 1:
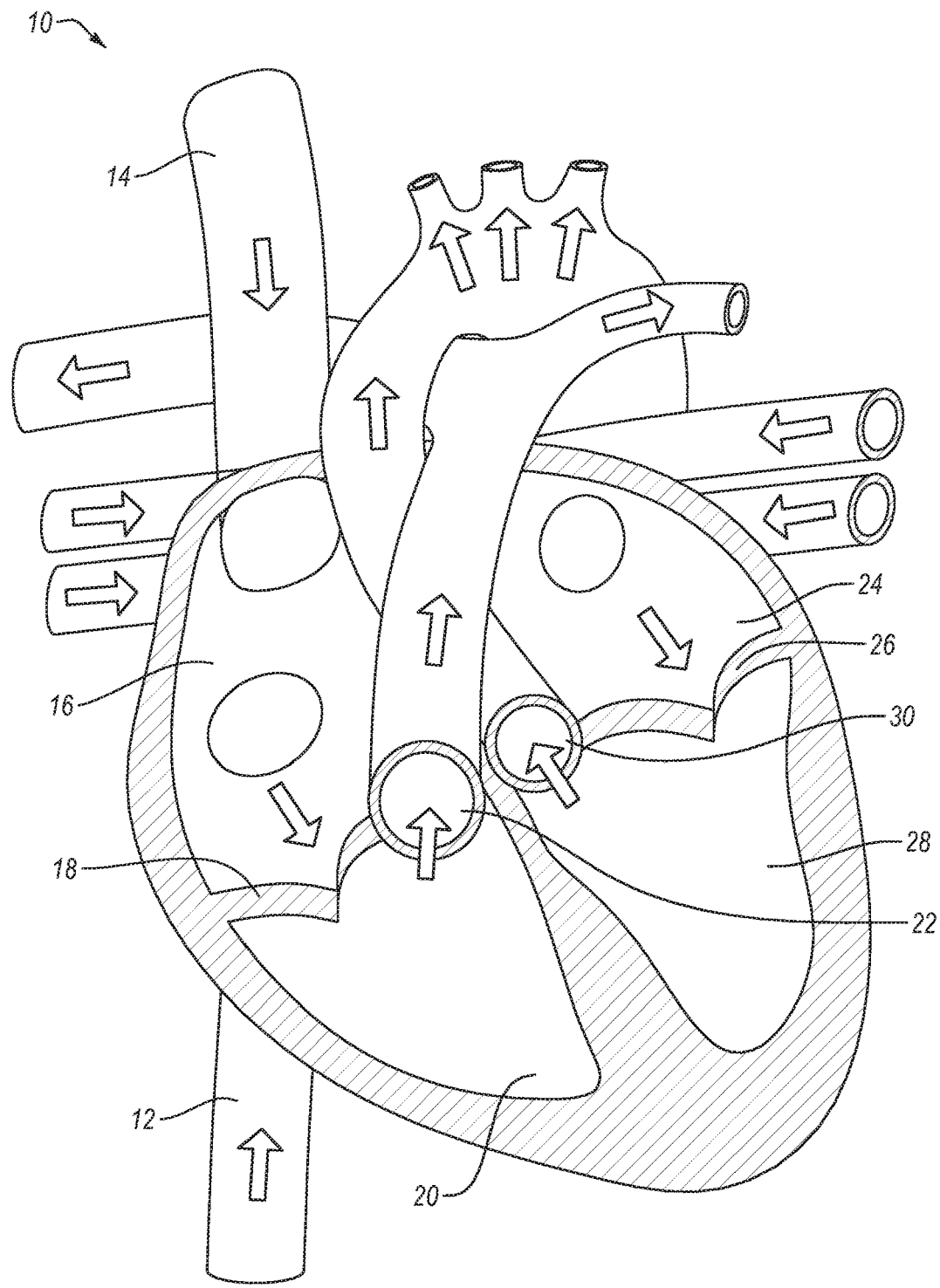
FIG. 1 illustrates a human heart showing normal blood flow paths.

FIG. 1 illustrates a cross-sectional view of a heart 10 showing the normal blood flow path. Deoxygenated blood enters the right atrium 16 through the superior vena cava 14 and superior vena cava 12. During diastole, suction from expansion of the right ventricle 20 and contraction of the right atrium 16 forces blood from the right atrium 16 across the tricuspid valve 18 and into the right ventricle 20. During ventricular systole, blood is then forced from the right ventricle 20 through the pulmonary valve 22 and into the pulmonary arteries for delivery to the lungs. In a normally functioning heart, the tricuspid valve 18 closes during systole to prevent backwards movement of blood from the right ventricle 20 back into the right atrium 16. When a tricuspid valve is not functioning properly, it may fail to fully close such that some of the blood passes back across the tricuspid valve 18 and into the right atrium 16, rather than through the pulmonary valve 22.

Oxygenated blood returning from the lungs enters the left atrium 24, where it is then passed through the mitral valve 26 and into the left ventricle 28. During ventricular systole, the blood is then passed from the left ventricle through the aortic valve for delivery throughout the body. Similar to the right side of the heart, failure of the mitral valve 26 to fully close during ventricular systole leads to regurgitation of blood from the left ventricle 28 back into the left atrium 24. In some circumstances, problems related to mitral valve regurgitation or other issues with the left side of the heart also cause or are associated with structural issues on the right side of the heart, such as tricuspid valve regurgitation.

Figure 2:
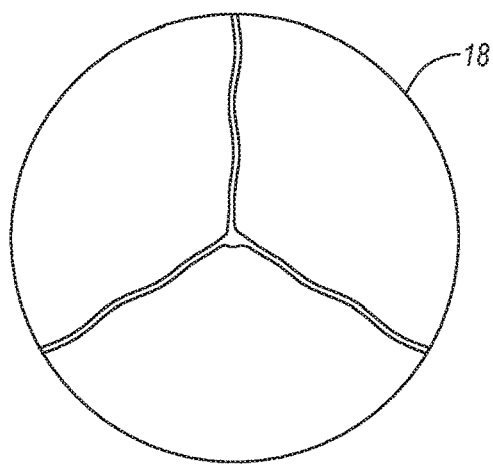
FIG. 2 illustrates a superior view of a normally functioning tricuspid valve in a closed position.
Figure 3:
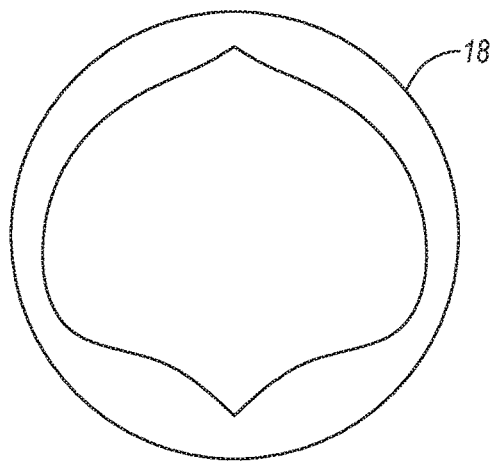
FIG. 3 illustrates a superior view of a tricuspid valve in an open position.
Figure 4:
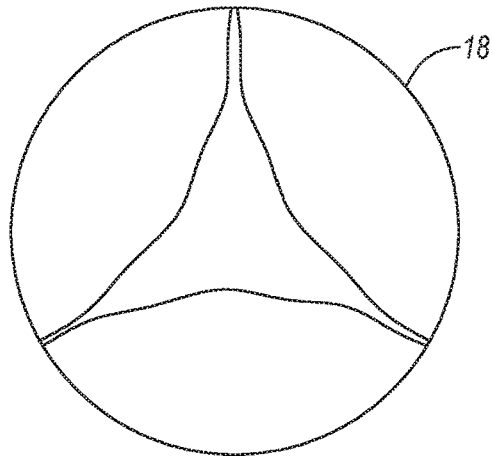
FIG. 4 illustrates a superior view of a malfunctioning tricuspid valve unable to properly close.

FIGS. 2-4 illustrate superior views of a tricuspid valve 18 in various states and positions. FIG. 2 illustrates a properly functioning tricuspid valve 18 in a closed position. A properly functioning tricuspid valve 18 takes this form during ventricular systole in order to block backflow of blood. As shown, when in the closed position, the three leaflets of the tricuspid valve 18 coapt to fully close the valve. FIG. 3 illustrates a properly functioning tricuspid valve 18 in an open position. When open, the leaflets of the tricuspid valve 18 extend downward into the right ventricle so that passage of blood through the tricuspid valve 18 is provided.

FIG. 4 illustrates a defective tricuspid valve 18 during ventricular systole. In contrast to the properly closed tricuspid valve of FIG. 2, the leaflets of the defective tricuspid valve are unable to fully coapt, leaving a passage through which regurgitant blood may pass. The inability to fully close may be due to defects to the leaflets themselves, or to defects to other structures of the heart which deform the tricuspid valve annulus or stretch the chordae tendineae, for example.

Figure 5:
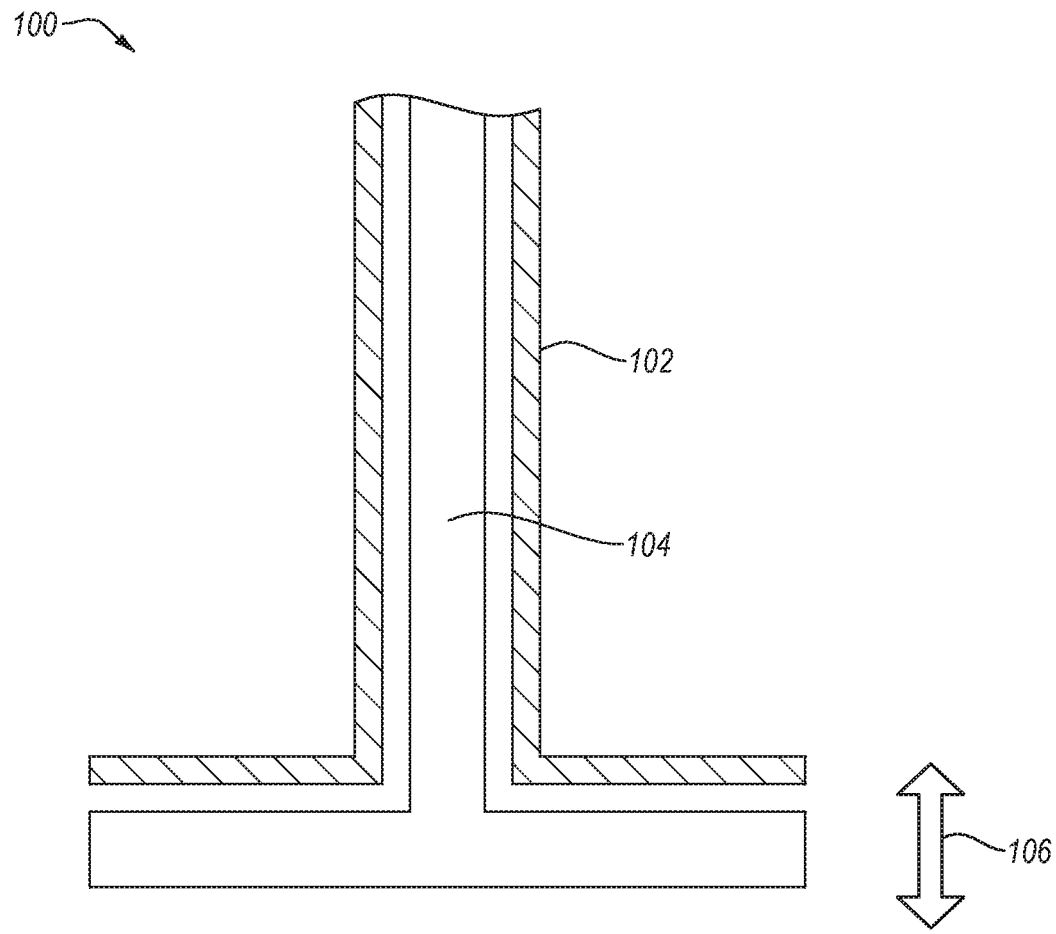
FIG. 5 illustrates an exemplary embodiment of a repair device that may be utilized to perform a tricuspid repair procedure as described herein.

FIG. 5 illustrates a cross-sectional view of an embodiment of a repair device 100 that may be utilized to reduce or eliminate regurgitation in a defective valve. The illustrated embodiment includes a proximal member 102 and a distal member 104 disposed within the proximal member 102 and configured to be axially translatable relative to the proximal member 102. Each of the distal member 104 and the proximal member 102 include arms extending transversely from respective longitudinal axes. In the illustrated embodiment, for example, the distal member 104 and proximal member 102 are configured with T shaped cross sections. As indicated by arrows 106, the distal member 104 is translatable relative to the proximal member 102 such that the space between the arms of the distal member 104 and the proximal member 102 may be selectively expanded or reduced.

As explained in more detail below, the repair device 100 may be utilized to grasp tissue between the respective arms of the distal member 104 and proximal member 102 by positioning the distal member 104 on a first side of the targeted tissue, with the proximal member 102 positioned on the opposite side of the targeted tissue, and translating the distal member 104 relative to the proximal member 102 to reduce the space between the arms of the distal member 104 and proximal member 102 to grasp the targeted tissue therebetween.

Figure 6:
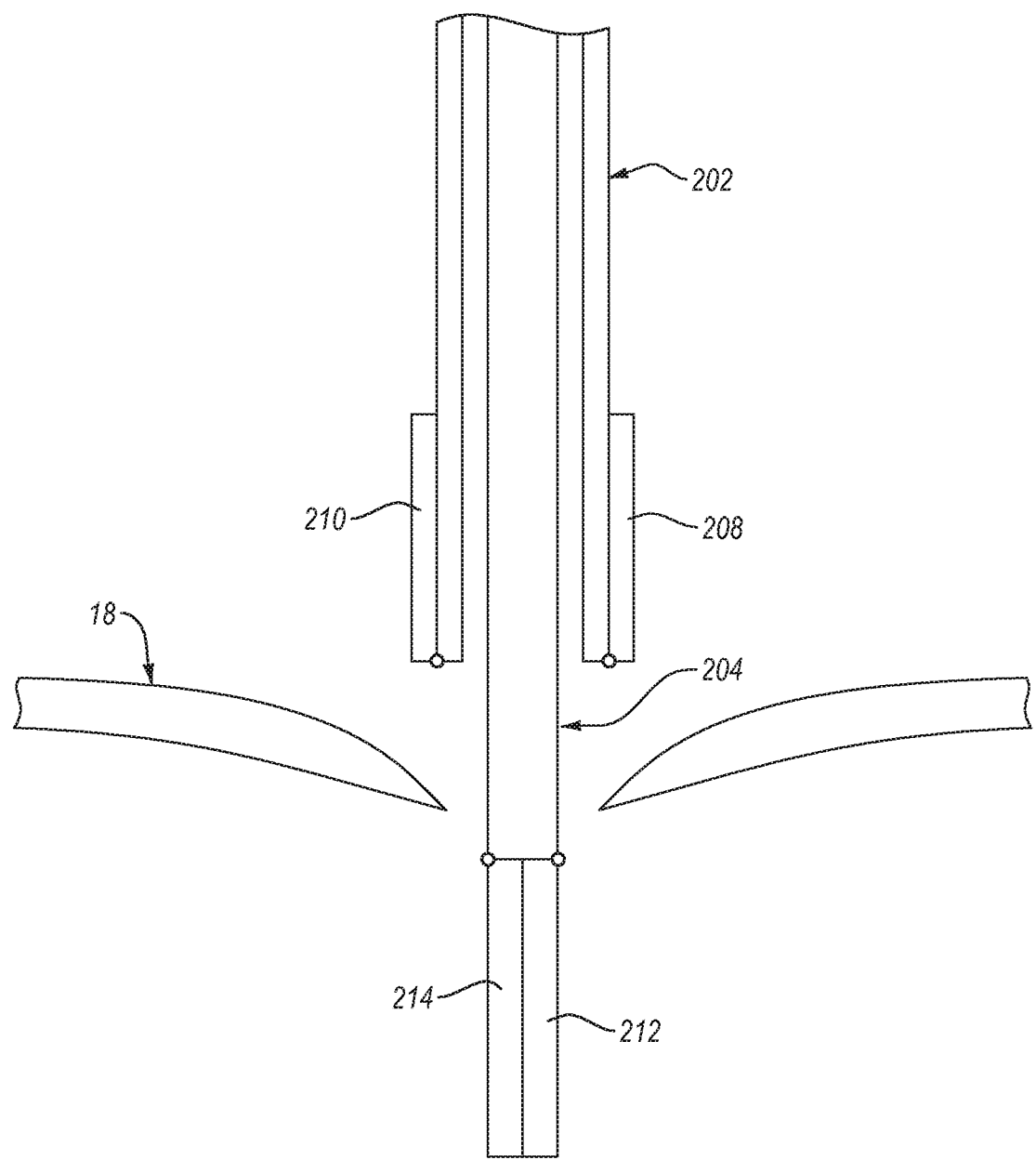
FIGS. 6-8 illustrate another embodiment of a repair device that may be utilized to perform a tricuspid repair procedure as described herein, showing deployment of extendable arms of the device and grasping of leaflet tissue therebetween.
Figure 7:
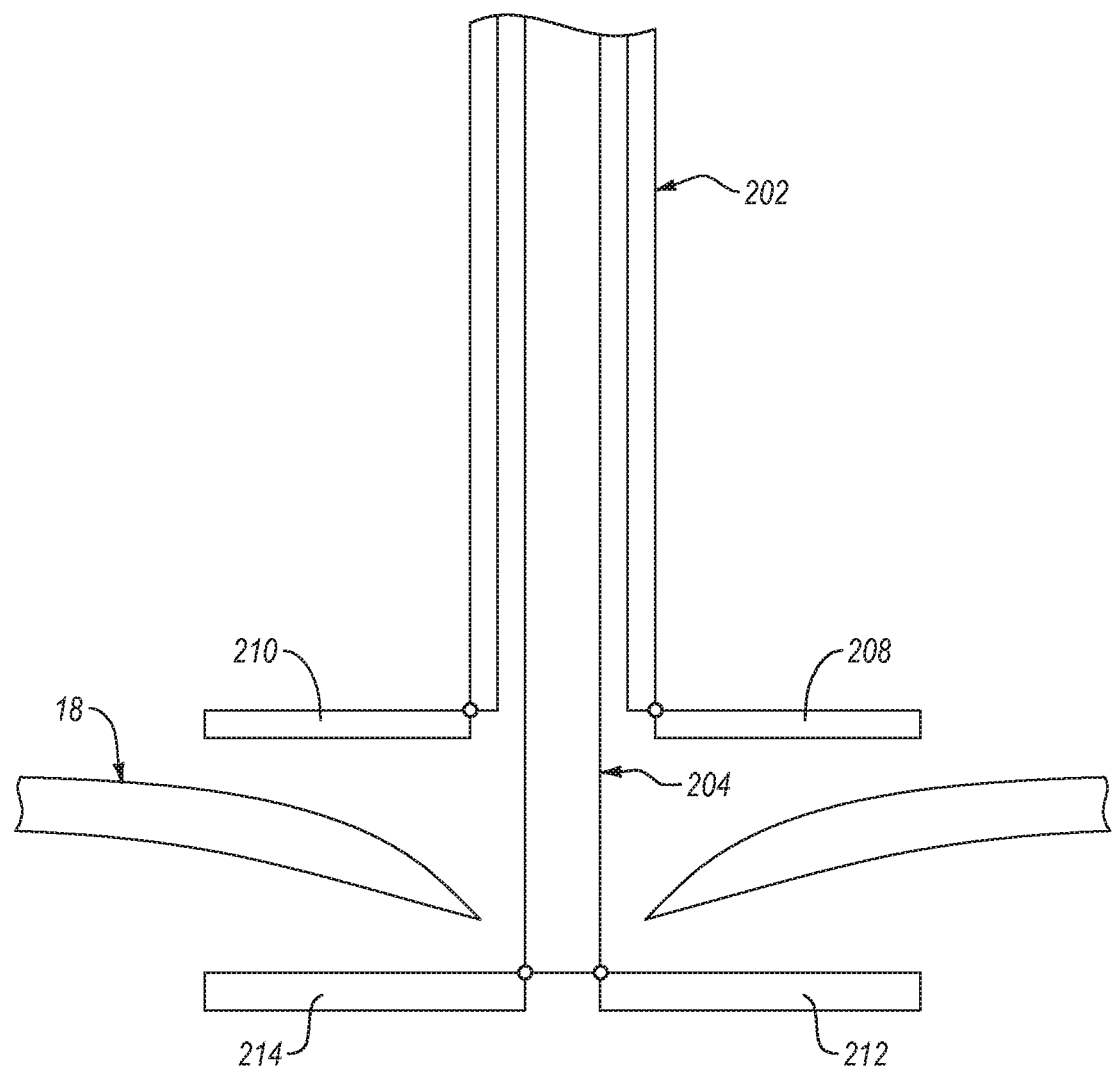
Figure 8:
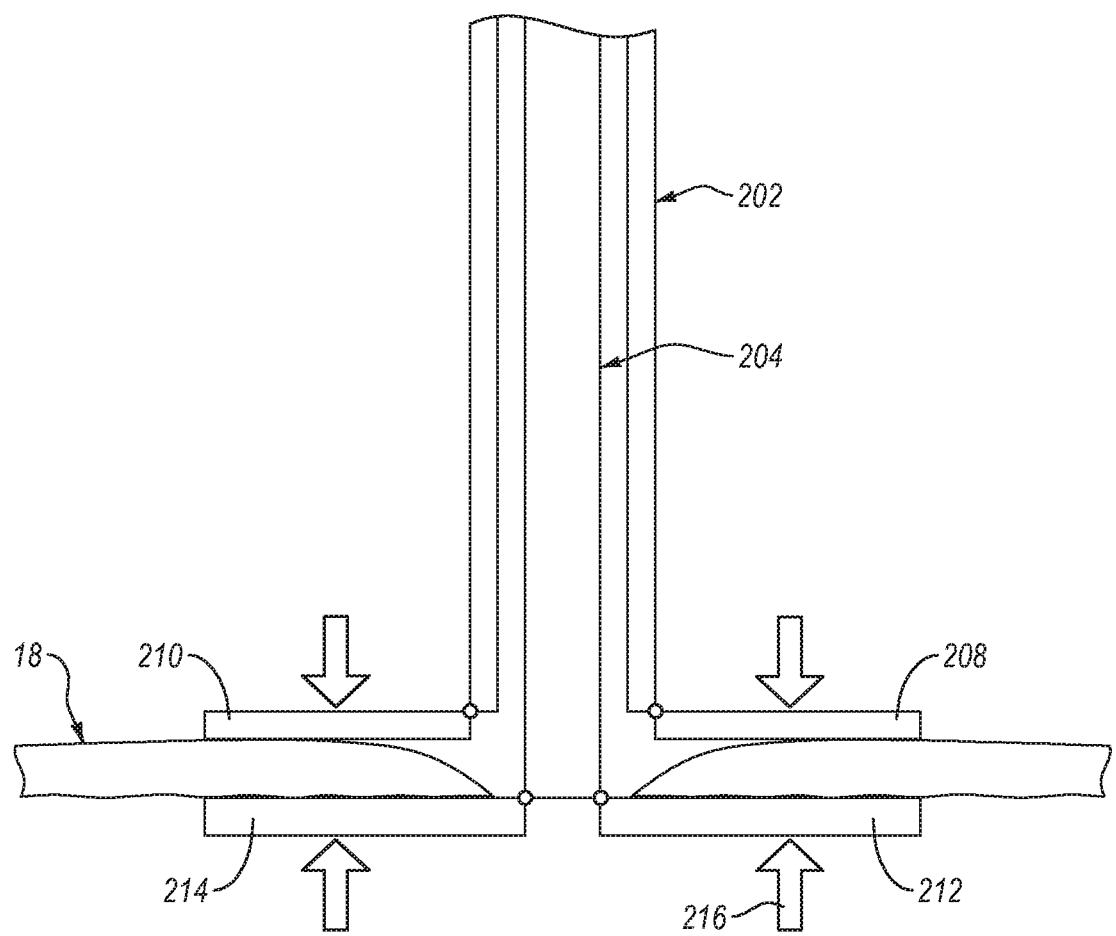

FIGS. 6-8 depict another embodiment of a repair device and an exemplary method for deploying a repair device to grasp tricuspid valve tissue for repair of a regurgitant tricuspid valve. FIG. 6 illustrates a repair device including a distal member 204 positioned within a proximal member 202 and extending out of and distally beyond a distal end of the proximal member 202. In the illustrated embodiment, the distal member 204 is translatable relative to the proximal member 202 such that the distal member 204 may be selectively extended distally or retrieved proximally relative to the proximal member 202.

In some embodiments, the repair device is delivered to the targeted tricuspid valve 18 by positioning the repair device in the right atrium, superior to the tricuspid valve 18, and extending the distal member 204 through the tricuspid valve 18 into the right ventricle. For example, the repair device may be delivered via a transfemoral approach so that the device passes through the inferior vena cava into the right atrium. Alternatively, the device may be delivered through a transjugular approach, transapical approach, or other approach.

Although the example depicted in FIGS. 6-8 is related to an approach in which the device is delivered to the right atrium and positioned superior to the tricuspid valve prior to deployment (e.g., through a transfemoral approach), it will be understood that the described principles and features may be applied to other approaches. For example, in a transapical approach, the repair device may be inserted into the right ventricle and be positioned inferior to the tricuspid valve. In the illustrated example, the repair device is deployed by extending the distal member 204 from the right atrium through the tricuspid valve 18 and into the right ventricle. It will be understood that from an inferior approach, the repair device may be deployed by extending the distal member 204 from the right ventricle through the tricuspid valve and into the right atrium.

As shown in FIG. 6, the proximal member 202 includes extendable arms 208 and 210, and the distal member 204 includes extendable arms 212 and 214. FIG. 6 illustrates the arms 208, 210, 212, and 214 in a retracted or collapsed position, providing the device with a low profile for delivery to the targeted tricuspid valve 18. In the illustrated embodiment, the extendable arms 208, 210, 212, and 214 are coupled to the axial bodies of the proximal member 202 and distal member 204, respectively, through a hinged attachment to enable actuation from the retracted position to an extended position. Alternatively, or additionally, one or more arms may be provided with the ability to selectively extend and retract through use of spring biasing and/or tension wire controls (e.g., one or more tension wires extending from a respective arm to a proximal handle/control element).

In some embodiments, the distal member 204 and/or proximal member 202 may be delivered in a sheathed configuration such that the corresponding arms, which are biased toward an expanded position, are held in a collapsed position by the sheath. The arms may then be selectively opened to the expanded position by retracting the corresponding sheath and/or pushing the respective member out from the sheath. The arms may be retracted to a collapsed position by repositioning the corresponding sheath over the arms to force them back into the retracted position.

As shown in FIG. 6, the distal member 204 may be positioned so as to pass through the plane of the tricuspid valve 18 and be positioned on a ventricular side of the valve, while the proximal member 202 remains on the atrial side of the valve. As shown in FIG. 7, the extendable arms 208, 210, 212, and 214 may then be opened to the extended position so that arms 208 and 210 of the proximal member 202 remain on the atrial side of the valve 18 and arms 212 and 214 remain on the ventricular side of the valve 18. As shown in FIG. 8, the distal member 204 may then be proximally retracted and/or the proximal member 202 may then be distally extended so as to bring the proximal (atrial side) arms 208 and 210 closer to the distal (ventricular side) arms 212 and 214 so as to grasp the tricuspid valve tissue 18 therebetween, as indicated by the arrows 216. In some embodiments, one or more of the arms 208, 210, 212, and 214 may include tines, hooks, protrusions, or other structures to enhance tissue grasping.

As shown, the proximal arms 208 and 210 are each substantially aligned with a corresponding distal side arm 212 and 214 to form an arm pair. In the illustrated embodiment, the proximal arm 208 and the distal arm 212 form a first arm pair, and the proximal arm 210 and distal arm 214 form a second arm pair. Additional examples of repair devices are provided in U.S. Pat. No. 7,666,204, which is incorporated herein by reference in its entirety. One or more of the clip device components and/or features described therein may be utilized for grasping tricuspid valve leaflet tissue as part of a tricuspid valve repair procedure described herein.

Figure 9:
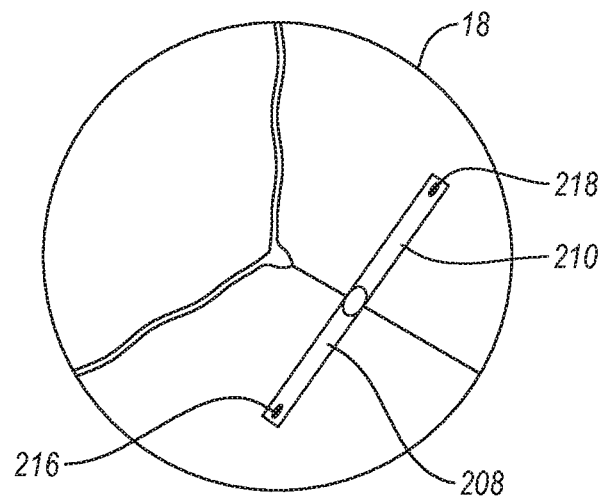
FIGS. 9 and 10 illustrate a superior view of a tricuspid valve showing a repair procedure using the repair device of FIGS. 6-8 to tie the leaflets of the tricuspid valve together to bring them closer together.
Figure 10:
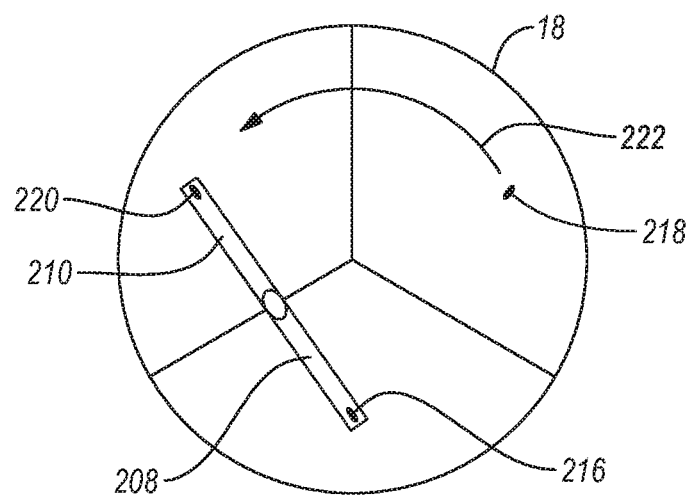

FIGS. 9 and 10 illustrate superior views of the tricuspid valve 18 showing deployment of any of the repair devices described herein in order to affix the tricuspid valve leaflets so as to reduce or prevent regurgitation through the tricuspid valve 18. Referring to FIG. 9, a first leaflet and a second leaflet of the tricuspid valve 18 may be grasped according to the procedure illustrated by FIGS. 6-8 or through another grasping process. From the superior view of FIG. 9, the proximal arms 208 and 210 of the proximal member are shown extending across the first and second leaflets so that a first end of the proximal member is located on the first leaflet at a first engagement point 216, and a second end of the proximal member is located on the second leaflet at a second engagement point 218 (i.e., so that the first arm pair is located at the first engagement point 216 and the second arm pair is located at the second engagement point 218).

From this position, one or more suture lines are passed from the first engagement point 216 to the second engagement point 218, or vice versa, to tie the first and second leaflets together. For example, one or more suture lines may be tied or otherwise attached (e.g., using buttons, anchors, pledgets, etc.) at the first engagement point 216, and passed to the second engagement point 218 where they may be likewise attached. Alternatively, one or more suture lines may be anchored at or tied to the second engagement point 218, but not passed to or from the first engagement point 216.

In some embodiments, one or more suture loops are attached at the first and/or second engagement points. For example, one or more suture lines may be passed from the first engagement point 216 to the second engagement point 218 where they are passed through a suture loop attached at the second engagement point 218. The one or more sutures may then be further routed to other areas of the tricuspid valve 18, as described in more detail below.

In alternative implementations, one or more suture lines may be anchored to one of the engagement points but not passed between the first and second engagement points 216 and 218. For example, one or more suturing lines may be attached (e.g., using buttons, anchors, pledgets, or other anchoring structures) at the second engagement point 218. The first and second leaflets are not sutured together, but the one or more suture lines anchored to the second leaflet at the second engagement point 218 are subsequently passed to the third leaflet to tie the second leaflet to the third leaflet. The one or more suture lines may be passed to the third leaflet in this manner by a pivoting motion of the repair device, as shown in FIG. 10.

As shown in FIG. 10, the repair device is then pivoted so that the second arm pair is pivoted about a pivot point to position the second end at the third leaflet. For example, as indicated by arrow 222 in the illustrated embodiment, the first engagement point 216 is used as a pivot point, and the second arm pair is pivoted so that the second arm pair is located on the third leaflet at a third engagement point 220. In some embodiments, one or more suture lines may be passed from the second engagement point 218 to the third engagement point 220 to tie the second leaflet to the third leaflet. Additionally, in some implementations, one or more suture lines may be passed from the third engagement point 220 to the first engagement point 216 to tie the third leaflet to the first leaflet.

In some embodiments, one or more suture lines are anchored at or threaded through the leaflet tissue at through least two of the various engagement points 216, 218, and 220 to form a suture lasso. Additionally, or alternatively, one or more suture lines are passed through one or more suture loops positioned at the engagement points 216, 218, and/or 220. In some embodiments, one or more sutures are tied to the first leaflet at the first engagement point 216 then passed through suture loop(s) at engagement point 218 (and in some embodiments passed additionally through engagement point 220), or are tied/anchored to the second leaflet at the second engagement point 218 then passed through suture loop(s) at engagement point 220. The one or more suture lines are then tightened to bring the leaflets of the tricuspid valve 18 closer together to reduce or eliminate regurgitation through the valve. In some embodiments, one or more sutures are tied at the first engagement point 216, then passed to both the second engagement point 218 and third engagement point 220 before being passed back to the first engagement point 216 to tie all three leaflets together.

The various engagement points 216, 218, and 220 may be positioned relative to one another so as to provide a desired degree of tightening and/or a desired amount of valve closure when the leaflets are cinched closer together with a suture lasso. Further, the suture lasso may be tightened so as to provide a desired degree of closure to the leaflets. For example, in a procedure where a targeted tricuspid valve has a relatively greater degree of structural deformity, a suture lasso may be tightened to a greater degree and/or one or more engagement points may be positioned relatively further from the valve annulus and relatively closer to a respective leaflet margin. In contrast, in a procedure where a targeted tricuspid valve has a relatively lower amount of structural deformity, the suture lasso may be tightened to a lesser degree and/or one or more engagement points may be positioned relatively closer to the valve annulus and further from a respective leaflet margin.

Figure 11:
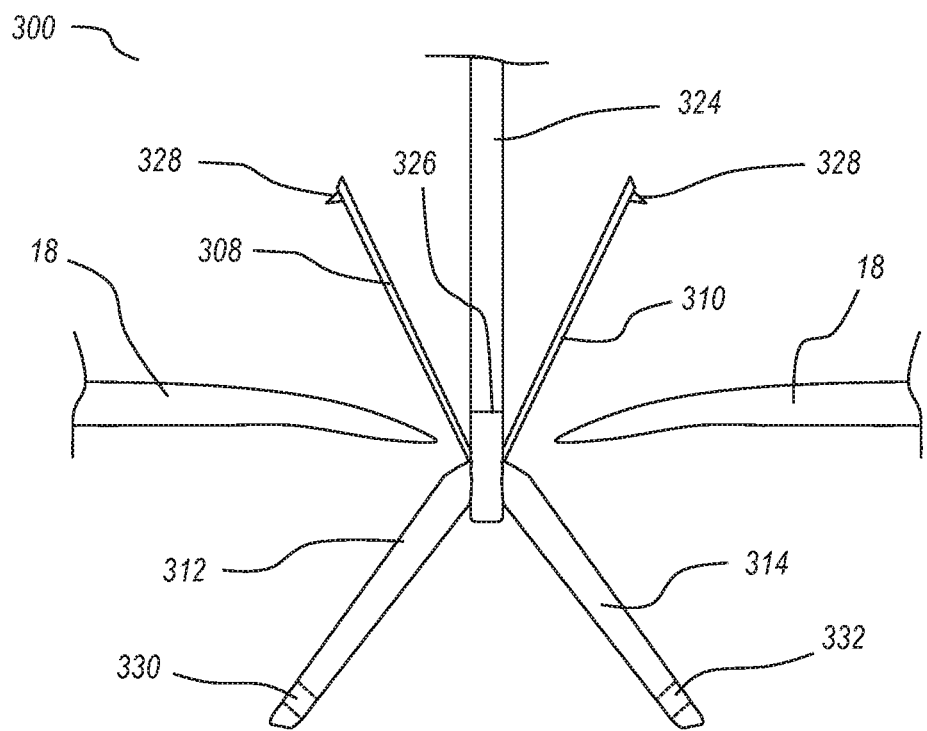
FIGS. 11 and 12 illustrate a side view of another exemplary embodiment of a clip device that may be utilized to perform a tricuspid repair procedure, showing grasping of two adjacent leaflets of a tricuspid valve using the device.
Figure 12:
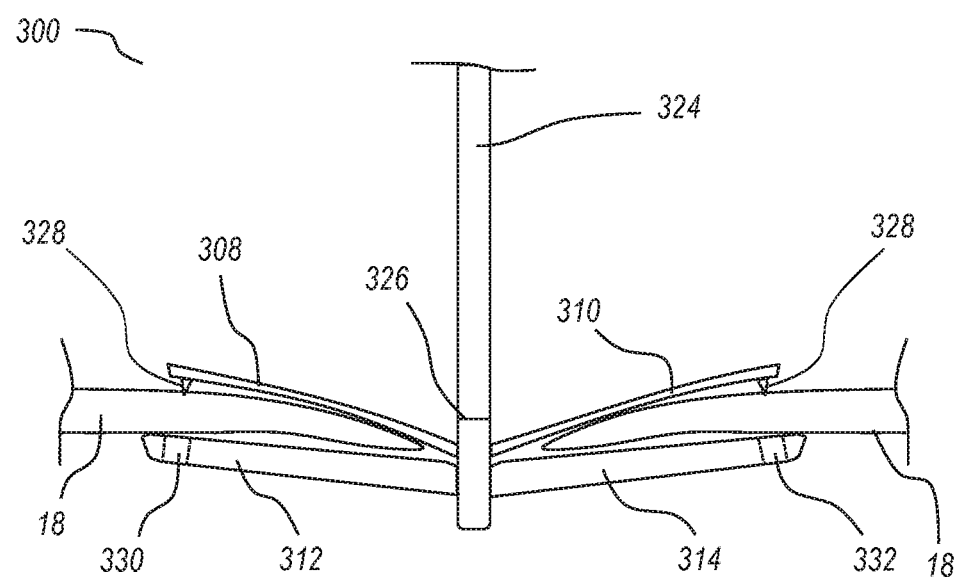

FIGS. 11 and 12 illustrate an exemplary embodiment of a repair device configured as a clip device 300, which may be utilized to grasp tricuspid valve leaflet tissue and to aid in suturing at least two adjacent leaflets to one another. The illustrated clip device 300 includes a pair of proximal arms 308 and 310, and a corresponding pair of opposing distal arms 312 and 314. The arms 308, 310, 312, and 314 are pivotally connected to the shaft 324 so as to be adjustable between a more open configuration (as shown in FIG. 11 where the arms are relatively more aligned to the axis of the shaft 324 and the device has a lower profile) and a more closed position (as shown in FIG. 12 where the proximal and distal arms are brought toward one another to grasp tissue therebetween). Proximal arms 308 and 310 can also include point elements 328 that can engage or penetrate into the valve tissue when proximal arms 308 and 310 are positioned against the tricuspid valve 18.

Typically, as shown in FIGS. 11 and 12, the clip device 300 is positioned with distal arms 312 and 314 disposed on the distal side of the tricuspid valve 18 (e.g., the ventricular side when a transfemoral approach is used) with the proximal arms 308 and 310 remaining on the proximal side of the valve (e.g., atrial side). The distal arms 312 and 314 are then positioned against the leaflet tissue of the valve 18 and the proximal arms 308 and 310 are then brought down to engage the leaflet tissue as shown in FIG. 12. After grasping, the arms 308, 310, 312, and 314 can be adjusted to move the clip device 300 into a closed position to bring grasped tissue closer together (see FIG. 24). The clip device may then be detached from the shaft 324 at detachment point 326 and left within the heart valve as an implant.

The clip device 300 may include one or more control lines, actuator rods, and/or other control mechanisms operably coupled to a handle to enable adjustments to the clip arms, detachment of the device, etc. The clip device 300 is preferably delivered using a transfemoral approach, although a tranjugular approach, transapical approach, or other suitable approach method may also be utilized.

The illustrated clip device 300 is also configured to enable suturing of grasped leaflet tissue. As shown, the distal arms 312 and 314 include through holes 330 and 332 for receiving suturing components. The proximal arms 308 and 310 also include corresponding through holes 350 and 352 (best seen in the superior view of FIG. 13). The corresponding through holes are formed so as to align when opposing arms are closed against tissue. As explained in more detail below, this allows suturing components to pass through a proximal through hole, through leaflet tissue, and into a distal through hole, in order to provide passage and/or positioning of one or more suture lines.

Figure 13:
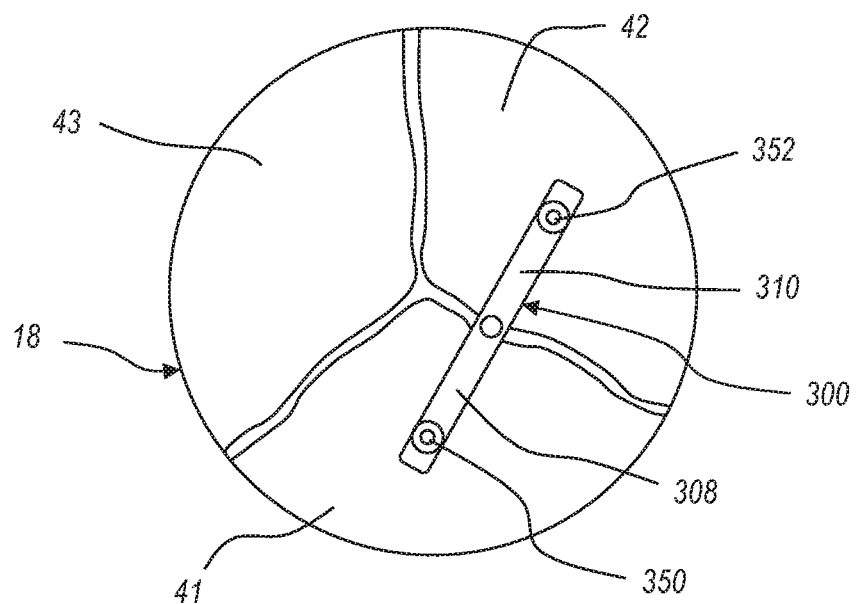
FIG. 13 illustrates a superior view of the clip device after grasping the two adjacent leaflets.

FIG. 13 illustrates a superior view of the clip device 300 that has grasped a first leaflet 41 and second leaflet 42 of the tricuspid valve 18. From this view, the proximal arms 308 and 310 are visible, as well as associated through holes 350 and 352 which provide passage through the proximal arms 308 and 310 to the underlying leaflet tissue. After leaflet tissue has been grasped in this manner, a suturing procedure can be carried out using the repair device 300 to tie two or more of the leaflets together.

Figure 14:
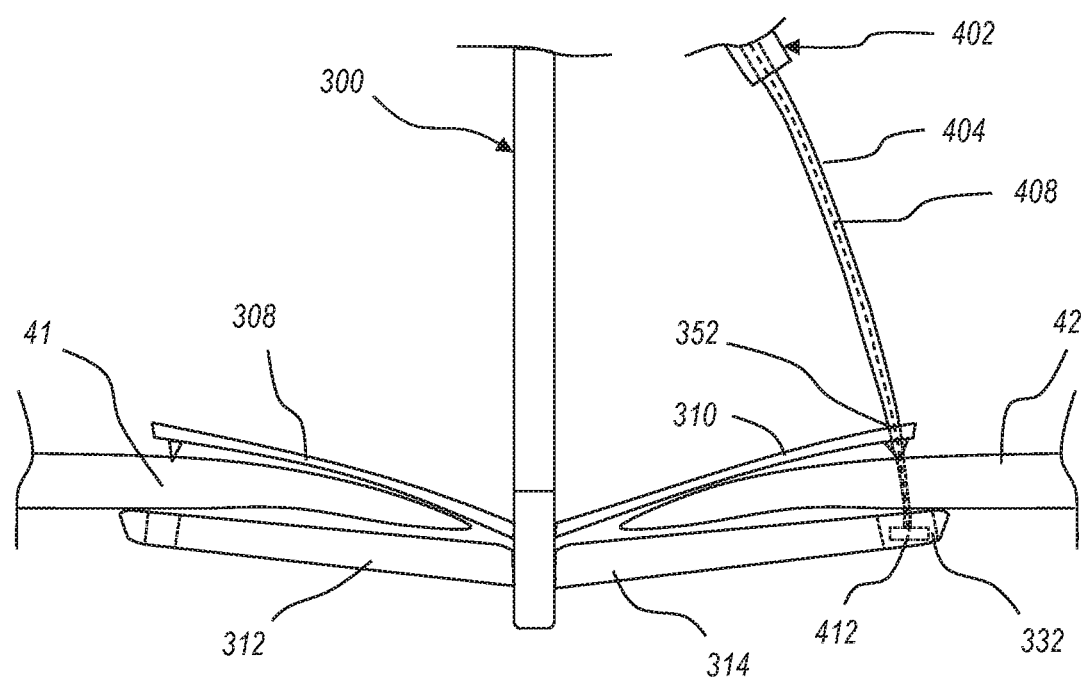
FIGS. 14 to 16 illustrate side views of the clip device showing the deployment of a suture line in a valve leaflet using a suturing catheter.

FIG. 14 illustrates, in side view, the same grasping position shown in FIG. 13. While the first and second leaflets 41 and 42 are grasped by the clip device 300, a suturing catheter 402 is routed to the vicinity of the tricuspid valve. The suturing catheter 402 may be routed through a tranjugular approach or transfemoral approach (e.g., using the femur opposite from the one used for transfemoral delivery of the clip device 300). The illustrated embodiments show a transjugular approach where the suturing catheter 402 is positioned on the proximal side of the clip device 300 (e.g., on the atrial side) and passing one or more suture lines through leaflet tissue from the proximal side to the distal side, but it will be understood that the same components and principles of operation may be utilized by positioning the suturing catheter 402 on the distal side of the clip device 300 and passing one or more suture lines through from the distal side to the proximal side.

As shown in FIG. 14, a first suture deployment catheter 404 is extended from the suturing catheter 402, and is extended to the proximal arm 310. The first suture deployment catheter 404 is positioned through the proximal through hole 352, the second leaflet 42, and into the corresponding distal through hole 332. A first suture line 408 (or optionally two or more suture lines) is associated with the first suture deployment catheter 404 so that as the first suture deployment catheter 404 is passed from one side of the leaflet 42 to the other, the first suture line 408 is also passed through the leaflet 42. In some implementations, a guide wire can first be passed out of the suturing catheter 402, through the proximal through hole 352, through the leaflet 42, and into the distal through hole 332 prior to moving the first suture deployment catheter 404, in order to establish a guided path for the first suture deployment catheter 404.

In the illustrated embodiment, the first suture line 408 includes at a distal end a first suture anchor 412. The first suture anchor 412 can be a pledget, button, bight or bundle or suture, or other structure capable of holding position against the leaflet 42 to prevent movement or tearing through the leaflet 42 when tightening tension is applied to the first suture line 408. In some embodiment, the first suture anchor 412 is flexible enough to bend and/or fold to a lower profile shape when passed through the leaflet 42, and is capable of expanding and/or folding into a larger profile shape once passed to the distal side of the leaflet 42.

Figure 15:
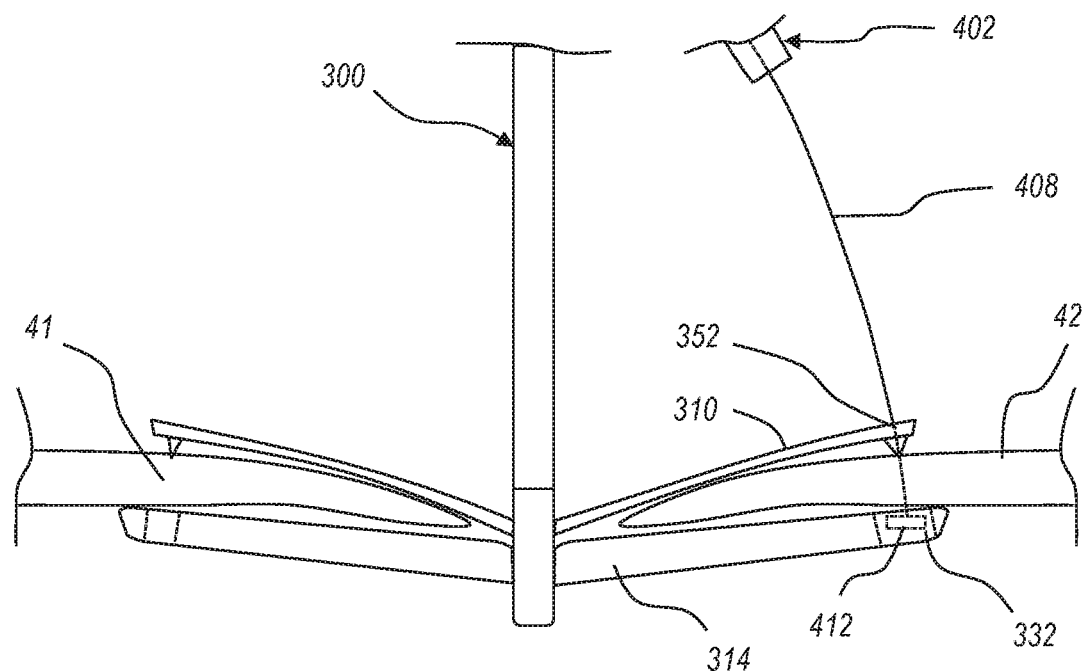

After deploying the first suture line 408, the first suture deployment catheter 404 is retracted, leaving the first suture line 408 deployed in the leaflet 42, as shown in FIG. 15. From this position, the clip device 300 can be selectively actuated to allow one end of the clip device 300 to be moved to another leaflet, while the other end of the clip device 300 remains anchored in place, thereby allowing another leaflet to be sutured and tied to the already sutured leaflet 42.

Figure 16:
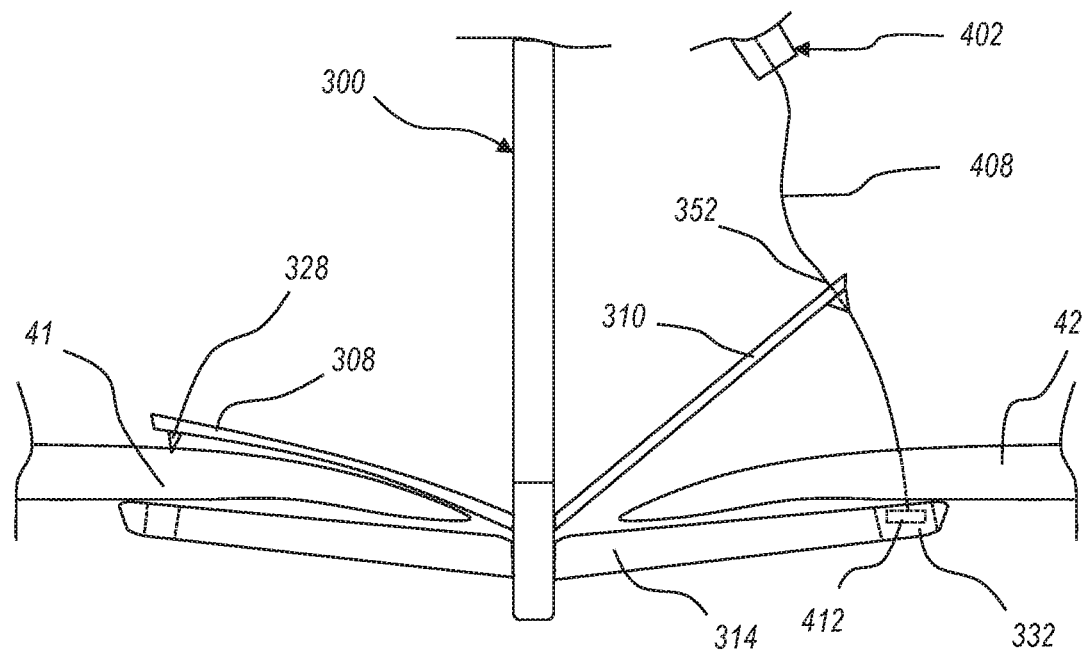

As shown in FIG. 16, the proximal arm 310 is lifted from the leaflet 42. The first suture line 408 is still deployed/anchored to the leaflet 42 and still passes through the proximal arm 310. The opposite proximal arm 308 is held in a closed position against leaflet 41 so that the point element 328 of the proximal arm 308 can act as a pivot point for moving, via a pivoting motion, the clip device 300 from the previous position (in which the proximal arm 310 and distal arm 314 were positioned on either side of leaflet 42) to a new position in which the proximal arm 310 and distal arm 314 are positioned on either side of adjacent leaflet 43. In some implementations, the distal arm 314 may be additionally moved away from the leaflet 42. However, in a typical application, inherent fluctuations in leaflet position will allow the leaflet 42 to be freed simply by lifting the proximal arm 310.

Figure 17:
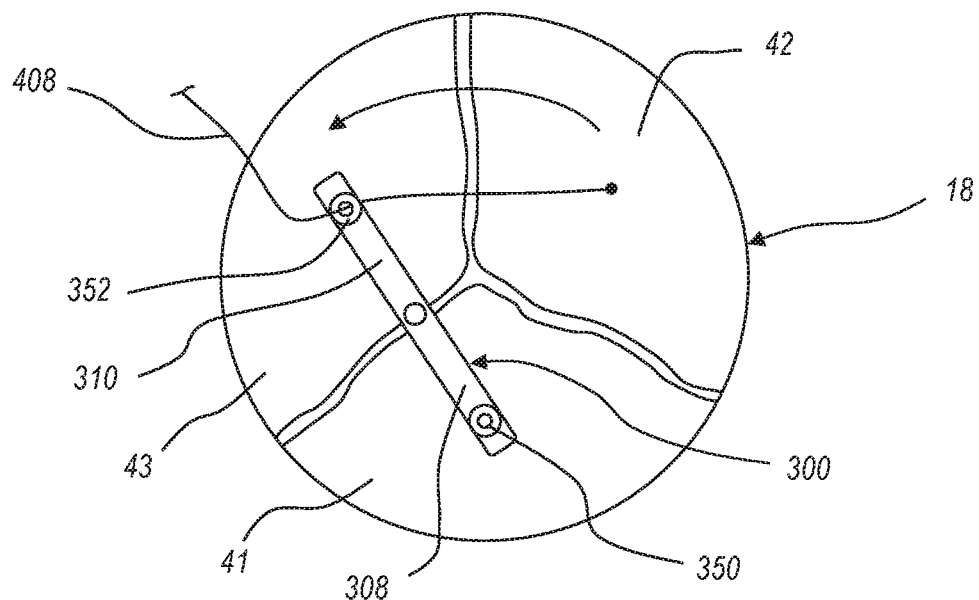
FIG. 17 illustrates a superior view of the clip device after a pivot procedure to grasp another leaflet of the tricuspid valve.

FIG. 17 illustrates a superior view of the tricuspid valve 18 showing the clip device 300 after the pivoting motion. As shown, the proximal arm 308 remains grasped against the first leaflet 41, while proximal arm 310 has been swung from the second leaflet 42 to the third leaflet 43. At this position, the proximal arm 310 and/or corresponding distal arm 314 is/are adjusted to grasp the third leaflet 43. As shown, the first suture line 408 now extends from the second leaflet 42, where it is anchored at engagement point 318, to the third leaflet 43, where it is held in place by the proximal arm 310. The free end of the first suture line 408 passes up through the through hole 352 and into the suturing catheter 402 (not shown in this view).

Figure 18:
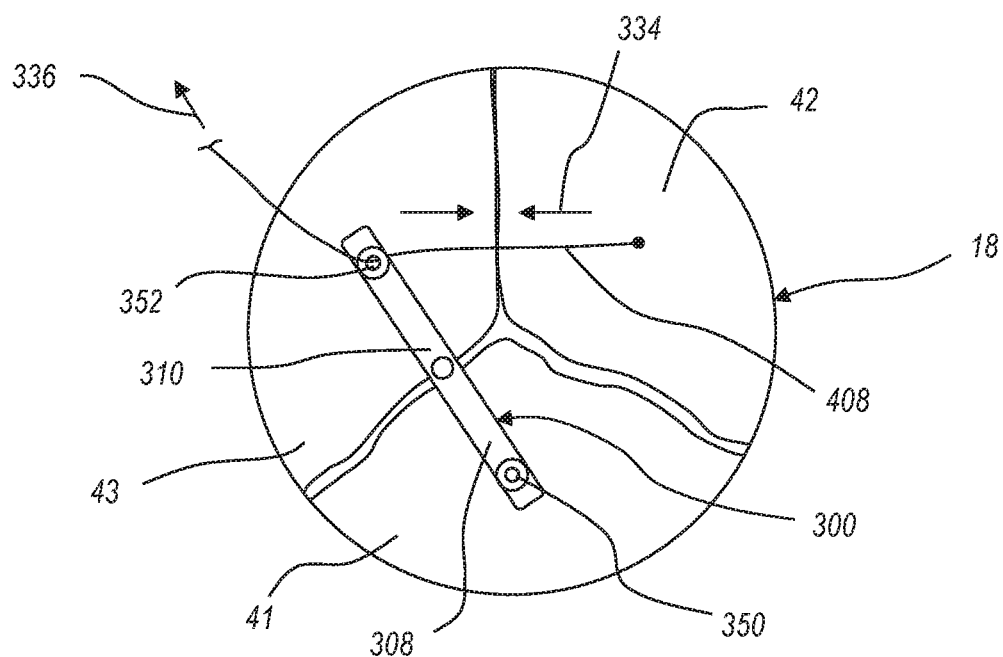
FIGS. 18 and 19 illustrate superior views of the clip device showing a cinching procedure using the deployed suture line to tie adjacent valve leaflets to one another.
Figure 19:
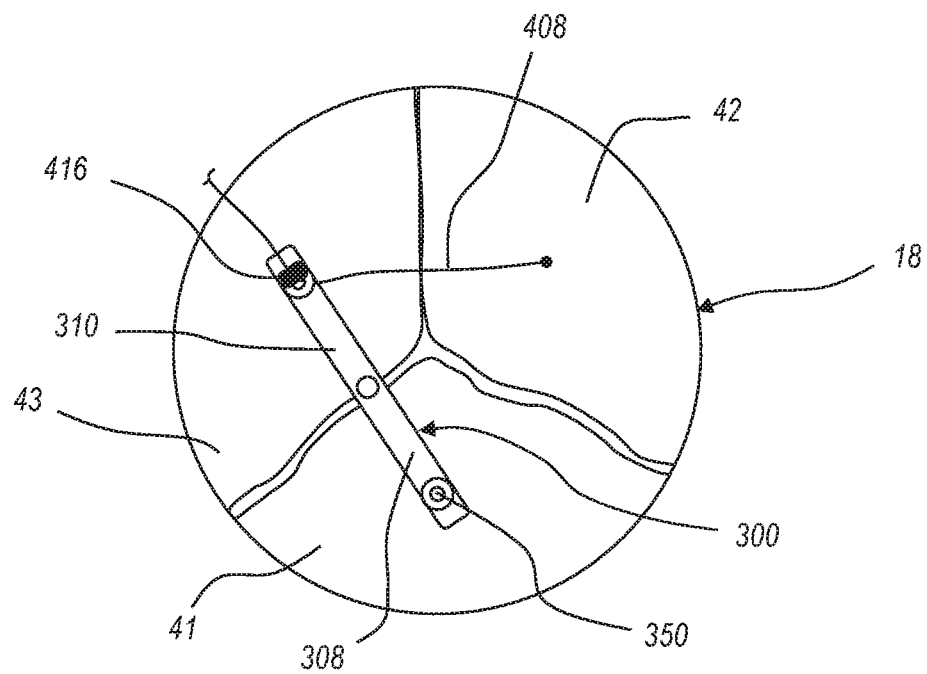

As shown in FIG. 18, the first suture line 408 can be tensioned (by pulling upward as indicated by arrow 336) to pull the second leaflet 42 and third leaflet 43 toward one another to a desired degree, as indicated by arrows 334. As shown by FIG. 19, a lock 416 may then be applied to maintain the length and/or tension of the first suture line 408 between the engagement point 318 and the proximal through hole 352.

The lock 416 may be a cinch, clamp, grommet, stop, or other fastening device capable of engaging against the suture line 408 to hold it in place and prevent it from slipping past the lock 416. In some embodiments, the lock 416 may be applied using the suturing catheter 402. In other embodiments, the lock 416 may form part of the clip device 300 and may be selectively actuated to engage against the suture line 408. In some embodiments, the suture line 408 may be slipped through a bight or otherwise knotted, in addition to or as an alternative to the lock 416, in order to hold the position of the suture line 408. Excess suture material may be cut from the device 300 prior to finishing the repair procedure.

Figure 24:
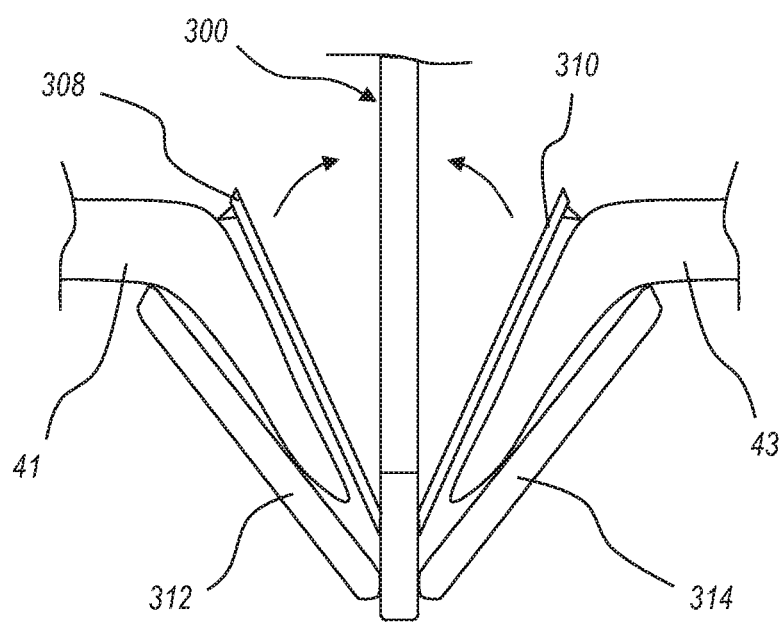
FIG. 24 illustrates closing of the clip device to bring the grasped valve leaflets closer to one another.

After tensioning the first suture line 408 to tie the second leaflet 42 and third leaflet 43 together, the clip device 300 may also be kept in the position shown to tie the third leaflet 43 and first leaflet 41 together. The clip device 300 may be adjusted toward a more closed position, as shown in FIG. 24 and as indicated by arrows 344, to effectively bring and hold together grasped tissue from the leaflets 43 and 41.

Figure 20:
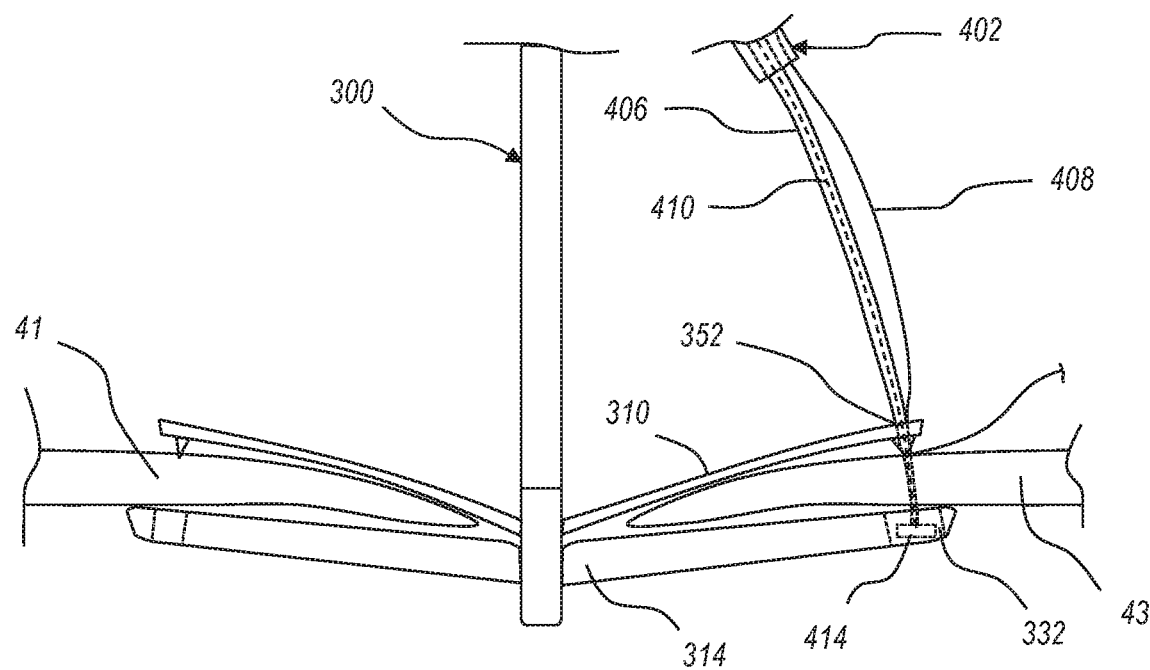
FIGS. 20 and 21 illustrate side views of the clip device showing an alternative repair procedure which deploys a second suture line into a second valve leaflet.

FIGS. 20 through 23 illustrate an embodiment in which a second suture line 410 is also deployed to tie targeted leaflet tissue together. FIG. 20 shows a side view of the repair device 300 after it has been pivoted to the position shown in FIG. 17. In this position, the first suture line 408 extends from the second leaflet 42 (not shown in this view) to the proximal arm 310, where it passes up through the through hole 352 and into the suturing catheter 402. As shown, a second suture deployment catheter 406 is extended from the suturing catheter 402. The second suture deployment catheter 406 deploys a second suture line 410 in a manner similar to that of the first suture deployment catheter 404 and first suture line 408, by passing through the through hole 352, through the third leaflet 43, and into the through hole 332. A second suture anchor 414 functions to hold the second suture line 410 in a manner similar to that of the first suture anchor 412 holding the first suture line 408.

Figure 21:
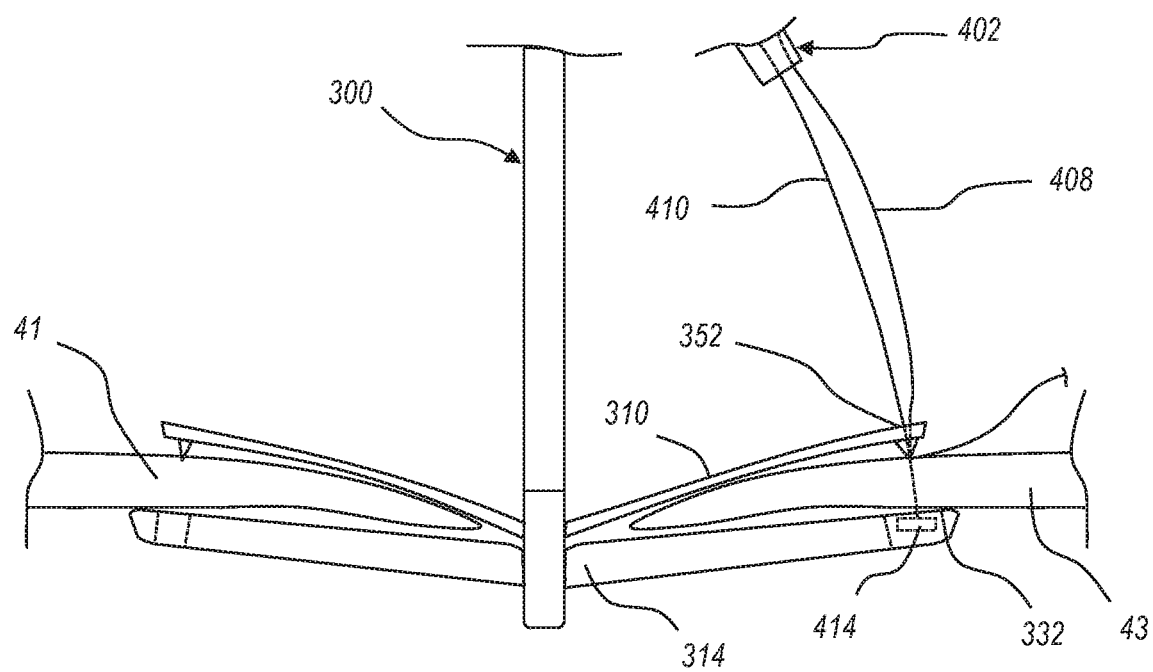
Figure 22:
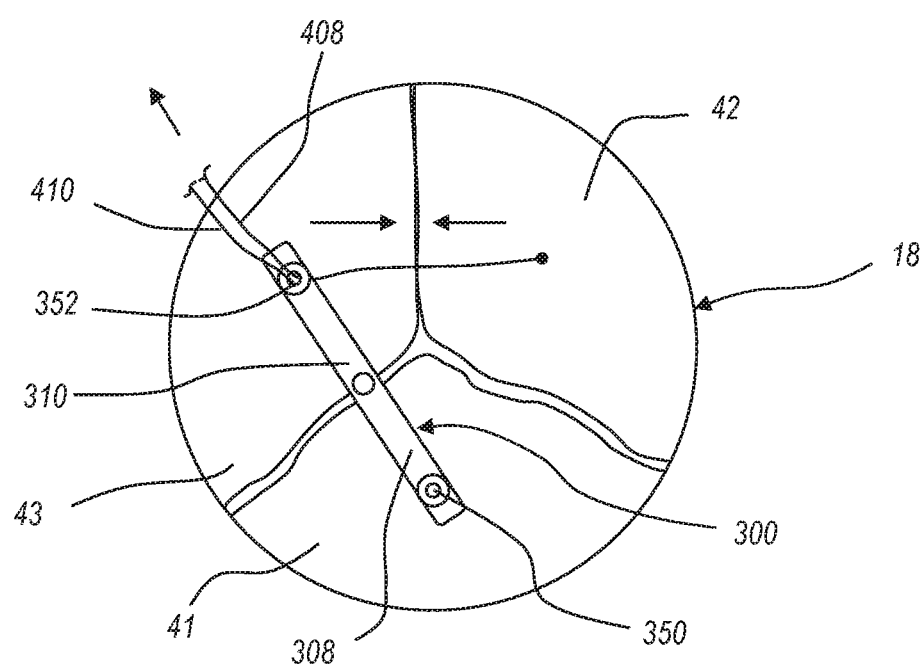
FIGS. 22 and 23 illustrate superior views of the clip device showing a cinching procedure utilizing the two deployed suture lines to tie adjacent valve leaflets to one another.
Figure 23:
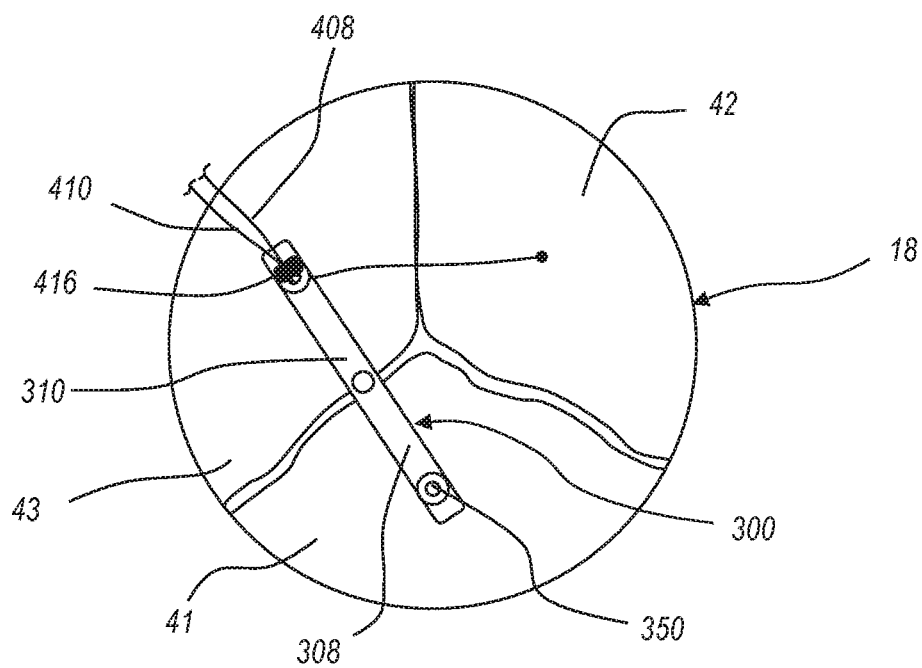

As shown in FIG. 21, the second suture deployment catheter 406 is then retracted, leaving the first and second suture lines 408 and 410 in position extending through the proximal arm 310 and into the suturing catheter 402. FIG. 22 shows a superior view of the repair device 300 in this position. From this position, tension may be selectively applied to the first and/or second suture lines 408, 410 to cinch and bring the second leaflet 42 and third leaflet 43 closer to one another. As shown in FIG. 23, a lock 416 may be deployed to maintain the positions of the first and second suture lines 408, 410. Excess suture material may be cut from the device 300. As described above, the clip device 300 may also be kept in place across the third leaflet 43 and first leaflet 41, and may be moved to a closed position as shown in FIG. 24 to effectively bring and hold together tissue from the grasped leaflets 43 and 41.

The combination of suturing a pair of adjacent leaflets and deploying the clip device 300 across another pair of adjacent leaflets beneficially provides effective repair of the tricuspid valve and effective reduction or elimination of regurgitant flow through the valve. In some embodiments, even further closing of a targeted tricuspid valve is achieved by adding a suture to the first leaflet 41 (e.g., by passing a suture deployment catheter through the proximal through hole 350 of the proximal arm 308 in a manner similar to that described above) and connecting that suture to the engagement point 318 of the second leaflet 42 to thereby stitch all three leaflets together.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to a repair device of FIGS. 5 to 8 may be combinable with any element described in relation to a clip device as illustrated by FIGS. 11 through 24.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A heart valve repair device, comprising:
   a pair of first arms;
   a pair of second arms disposed opposite the pair of first arms, one first arm of the pair of first arms and one second arm of the pair of second arms forming a first arm pair,
   wherein the pair of first arms and the pair of second arms are moveable between an open configuration in which the arms of the first arm pair are moved apart from one another and a closed configuration in which the arms of the first arm pair are brought toward one another to enable grasping of leaflet tissue therebetween,
   wherein the first arm pair includes a point element configured to engage against leaflet tissue to function as a pivot point about which a second arm pair pivots, the second arm pair including a set of through holes through which a line is passed to enable suturing of leaflet tissue grasped by the second arm pair; and
   wherein the second arm pair includes a lock configured to maintain a length or tension of the line.

2. The repair device of claim 1, wherein the second arm pair is configured to be adjustable independently from the first arm pair.

3. The repair device of claim 1, wherein the line comprises an anchor on an end of the line.

4. The repair device of claim 3, wherein each hole of the set of through holes is configured to accommodate the anchor on the line.

5. The repair device of claim 1, wherein each of the first arms is movable independently from the pair of second arms.

6. The repair device of claim 1, wherein one of the first arms is configured to pivot toward one of the second arms.

7. The repair device of claim 1, wherein one of the first arms is configured to translate towards one of the second arms in a longitudinal direction.

8. The repair device of claim 1, wherein the lock is selected from a group consisting of a cinch, clamp, and grommet.

9. The repair device of claim 1, wherein the lock is configured to engage against the line to hold the line in place.

10. A heart valve repair device, comprising:
    a pair of distal arms;
    a pair of corresponding proximal arms disposed opposite the pair of distal arms, each distal arm and corresponding opposite proximal arm forming an arm pair,
    wherein the pair of distal arms and the pair of proximal arms are moveable between an open configuration in which the pair of distal arms and the pair of proximal arms are moved apart from one another and a closed configuration in which the pair of distal arms and the pair of proximal arms are brought toward one another to enable grasping of leaflet tissue therebetween,
    wherein one of the arm pairs includes a point element configured to engage against leaflet tissue to function as a pivot point about which another arm pair rotates, the another arm pair including a through hole through which a suture line is passable to enable suturing of leaflet tissue grasped by the another arm pair; and
    wherein the another arm pair includes a lock configured to maintain a length or tension of the suture line.

11. The repair device of claim 10, wherein the another arm pair is configured to be adjustable independent of the arm pair.

12. The repair device of claim 10, wherein the suture line comprises an anchor on an end of the suture line.

13. The repair device of claim 10, wherein each arm of the pair of proximal arms is movable independently from each arm of the pair of distal arms.

14. The repair device of claim 10, wherein one of the pair of proximal arms is configured to pivot toward one of the pair of distal arms.

15. The repair device of claim 10, wherein one of the pair of proximal arms is configured to translate towards one of the pair of distal arms in a longitudinal direction.

16. The repair device of claim 10, wherein the lock is selected from a group consisting of a cinch, clamp, and grommet.

17. The repair device of claim 10, wherein the lock is configured to engage against the suture line to hold the suture line in place.

18. A heart valve repair system, comprising:
    a clip device, the clip device including:
      two distal arms;
      two proximal arms disposed opposite the two distal arms, one of the distal arms and one of the proximal arms forming a first arm pair and the other of the distal arms and the other of the proximal arms forming a second arm pair,
      wherein the distal arm and proximal arm of the first arm pair are moveable between an open configuration in which the distal arm and the proximal arm are moved apart from one another and a closed configuration in which the distal arm and the proximal arm of the first arm pair are brought toward one another to enable grasping of leaflet tissue therebetween, wherein at least the first arm pair includes a point element configured to engage against leaflet tissue to function as a pivot point allowing the second arm pair to rotate about the pivot point, the second arm pair including a set of through holes through which one or more suture lines are passable to enable suturing of leaflet tissue grasped by the second arm pair; and wherein the second arm pair includes a lock configured to maintain a length or tension of the one or more suture lines; and a suturing catheter having an internal lumen through which the one or more suture lines are extendable, the suturing catheter being configured to engage with the second arm pair to enable passage of the one or more suture lines through the leaflet tissue grasped by the second arm pair.

19. The repair system of claim 18, wherein the suturing catheter includes a suture deployment catheter which is extendable from the suturing catheter.

20. The repair system of claim 19, wherein the suture deployment catheter is configured to pass into the set of through holes and to pierce the leaflet tissue grasped by the second arm pair to deploy the one or more suture lines.

21. The repair system of claim 18, wherein each of the one or more suture lines include a distal anchor member which prevents the one or more suture lines from moving back through the leaflet tissue after being passed through the leaflet tissue.

22. The repair system of claim 21, wherein the distal anchor member comprises a pledget, button, or suture bight.

23. The repair system of claim 18, wherein each of the proximal arms comprises a through hole configured to accommodate the one or more suture lines.

24. The repair system of claim 23, wherein the point element comprises the through hole configured to accommodate the one or more suture lines.

25. The repair system of claim 18, wherein the lock is selected from a group consisting of a cinch, clamp, and grommet.

26. The repair system of claim 18, wherein the lock is configured to engage against the one or more suture lines to hold the one or more suture lines in place.

* * * * *